(12) United States Patent
Bendahmane et al.

(10) Patent No.: US 8,319,018 B2
(45) Date of Patent: Nov. 27, 2012

(54) GENETIC SYSTEM FOR CONTROLLING THE FLORAL DEVELOPMENT OF A DICOTYLEDON PLANT, AND IMPLEMENTATION IN DETECTION AND SELECTION PROCESSES

(75) Inventors: Abdelhafid Bendahmane, Le Coudray Montceaux (FR); Adnane Boualem, Cusset (FR); Mohamed Fergany, Le Caire (EG); Catherine Dogimont, Vedene (FR)

(73) Assignee: Institut National de la Recherche Agronomique, Paris (FR)

( * ) Notice: Subject to any disclaimer, the term of this patent is extended or adjusted under 35 U.S.C. 154(b) by 477 days.

(21) Appl. No.: 12/298,811

(22) PCT Filed: Apr. 30, 2007

(86) PCT No.: PCT/FR2007/051197
§ 371 (c)(1),
(2), (4) Date: Jul. 29, 2009

(87) PCT Pub. No.: WO2007/125264
PCT Pub. Date: Nov. 8, 2007

(65) Prior Publication Data
US 2009/0288214 A1 Nov. 19, 2009

(30) Foreign Application Priority Data
Apr. 28, 2006 (FR) ...................................... 06 51538

(51) Int. Cl.
*C12N 15/29* (2006.01)
*C12N 15/82* (2006.01)
*C12N 15/87* (2006.01)
*C12N 5/04* (2006.01)
*A01H 5/00* (2006.01)

(52) U.S. Cl. ... 800/298; 536/23.1; 536/23.6; 435/320.1; 435/410; 435/419

(58) Field of Classification Search .................. None
See application file for complete search history.

(56) References Cited

U.S. PATENT DOCUMENTS
2003/0154521 A1  8/2003  Taurick

FOREIGN PATENT DOCUMENTS
WO    8701905    4/1987

OTHER PUBLICATIONS

Noguera et al (2005, Theor. Appl. Genet. 110:714-720).*
Papadopoulou et al (2001, Hortscience 36(3):455).*
Boualem et al, Science (2008) 321:836-838.*
Papadopoulou et al (2005, Sexual Plant Reproduction 18(3):131-142).*
Lindstrom et al (1998, NCBI Accession No. AF049711).*
Papadopoulou Ekaterina et al., "Effect of modified endogenous ethylene production on sex expression, bisexual flower development and fruit production in melon (*Cucumis melo* L.)", Sexual Plant Reproduction, vol. 18, No. 3, Nov. 2005, pp. 131-142, XP 002408826.
Papadopoulou Ekaterini et al., "Influence of heterologous acc synthase gene on sex expression of melon", Hortscience, American Society of Horticultural Science, Alexadria, VA, US, vol. 36, No. 3, Jul. 25, 2001, p. 455, XP 008071541.
Noguera F J et al., "Development and mapping of a codominant SCAR marker linked to the andromonoecious gene of melon", Theoretical and Applied Genetics, vol. 110, No. 4, Feb. 2005, pp. 714-720, XP 002408832.
Silberstein et al., "Linkage map of *Cucumis melo* including phenotypic traits and sequence-characterized genes", Genome, vol. 46, No. 5, Oct. 2003, pp. 761-773, XP 008071831.
Yamasaki Seiji et al., "Hormonal regulation of sex expression in plants", Vitamins and Hormones, 2005, vol. 72, pp. 79-110, XP 008071798.
Ram Danger et al, "Inheritance of gynoecism in bitter gourd (*Momordica charantia* L.)", Jouranl of Heredity, vol. 97, No. 3, May 2006, pp. 294-295, XP 008071801.
Ye Bo-Ping et al., "Studies on a gynoecious-specific acc synthase gene in different sexual phenotypes of cucumber genome", Acta Botanica Sinica, Plenum/China Program, New York, US, vol. 42, No. 2, Feb. 2000, pp. 164-168, XP 008071543.
Witkowicz Justyna et al., "AFLP marker polymorphism in cucumber (*Cucumis sativus* L.) near isogenic lines differing in sex expression", Cellular and Molecular Biology Letters, University of Wrocaw. Institute of Biochemistry, Wrocaw, PL, vol. 8, No. 2, 2003, pp. 375-381, XP 008072069.
Mibus H et al., "Molecular characterization and isolation of the F/f gene for femaleness in cucumber (*Cucumis sativus* L.)", Theoretical and Applied Genetics, vol. 109, No. 8, Nov. 2004, pp. 1669-1676, XP 002408828.
Przybecki Zbigniew et al., "The isolation of CDNA clones from cucumber (*Cucumis sativus* L) floral buds coming from plants differing in sex", Cellular and Molecular Biology Letters, University of Wrocaw, Institute of Biochmistry, Wrocaw, PL, vol. 8, No. 2, 2003, pp. 421-438, XP 008071825.

* cited by examiner

Primary Examiner — Stuart F. Baum
(74) Attorney, Agent, or Firm — Young & Thompson

(57) ABSTRACT

A genetic system for controlling the type of floral development of a dicotyledon plant, includes the combination of two genetic control elements, respectively:
a first genetic control element (A/a) present in a dicotyledon plant, in the form of a dominant allele (A), and a recessive allele (a), and
a second genetic control element (G/g) present in a dicotyledon plant, in the form of a dominant allele (G), and a recessive allele (g),
provided that the first genetic control element has been artificially inserted into the dicotyledon plant. This system enables the sex of the flowers of dicotyledon plants to be controlled and/or modified.

13 Claims, 2 Drawing Sheets

SEQUENCE LISTING

```
<160> NUMBER OF SEQ ID NOS: 25

<210> SEQ ID NO 1
<211> LENGTH: 13380
<212> TYPE: DNA
<213> ORGANISM: Cucumis melo

<400> SEQUENCE: 1
tatacacatt ttgtaatgat aaaattagaa gactagttga ttaattgttt aggctttatt      60
atatattcat cataagtctt ttttgtagcc atttaggttt gttttcgtcg aattaatctt     120
```

```
ataaacacta ttttattcg taaattccgt tgctttctta tttactttat atcaatgctt      180
taaaacatca atctagtttt taaaaatcaa tatatatgtt tgcacacacc attattatcg      240
tatgttactc tatctattac tgacaaacgt tatgaaattt tattatattt gtaattatct      300
tttgcagttt tgtcatttaa aatcgttttt cttaaaagaa ttatgttgtt attttaaaat      360
tttggctaaa gaatcacgtg gagaattaga tatatcaaac ctttcatctt tgagatgaaa      420
gattacatca attactatta actaagctta ctttgataaa ttaaaatcat attaaaacaa      480
atagtccgta aaagaatata attttgaaaa actaaacagt catcaaacaa cgcgtgttag      540
cttttaatat atattatgat atgttaagtg aaaataaagt tgaagtgtat gaagccaaaa      600
gagaagtcgt tttcacttgt tgagttctaa tttctaggat ggttctatgt aaagtacttc      660
ctcttccaaa attggaatcc aactcactac ttataaacat catttattcg tcatcttaat      720
tacaatacca actcttattt ttgtctcatc tatcatcaca ctcactaatt aacattacca      780
ttatcttata tcatttttatg aactcattat ttaacaaata aatcacttaa aagtttaact      840
tcaaaaaaaa aaaggaagaa agaaagaagg tttgaaatta cactatttgc aattaattat      900
gttttatgaa aactttctaa tactttaatt ttatgtcgaa tcgtttgtcg aatcgtttct      960
cttttatcct actacaaaaa tattataaaa tgattataaa tggctaaaat atatagtatg     1020
tgtatttcat aaatttaaga aaatgttttc gaatacagtc aaatgaacta aaatatttac     1080
aaaaatataa caaaatttca tatgtatatc gaataaaatt taaaaatttg aagactaaat     1140
ttgtaatata attacatatt aaagtaattt ttagatgtgt gggtattata taataataat     1200
gttgggaagg tgagggcatg aggcagctgg agggataagg actagggatt gttttatatc     1260 cttttttcaca tttaattttt gatgctaatt aatttgttgc caatcatttc atcacttttt     1320
tttttttttt tggttctaat ttatttactt tatatggaaa ataaataaaa gaaaaatgaa     1380
agaaagaaaa aagtggtttt caaatcaata gaaaaaacaa acaactccaa ctttaatggc     1440
ttgaaaacaa atgcattcta aaattaaacc ttatgattga tttgatttttt attcccctttt     1500 tttacactttt tcattttcat cataattata tcttcagtta cctgtccacc aattacacca     1560
tcaaatgtgg attattggga ttcttttttt tttttttaag attatcttac ggctttcatt     1620
tttttcgtat ctttatgacg gtttgataga cgtaaaagtg gttattgtgt tatagagatt     1680
tgtattattt tgatattatg gaaggattcg tttgagtaaa attataaaaa tcagaggggt     1740
gtcgtttaaa aatgtaagta atccaacaca aaaaaataat tatcataaaa tgtaaaaaaa     1800
agggttagat tgaaaacaaa cgaaacaaat gagttttgta ttataaatcg acctaaaatg     1860
ttcaacccaa acatggatta cgatacgacc gattcatctc attacagctc atcgatccta     1920
aaaatgtgaa gagaagtatt ggatataatt attacttaaa aagataatag aaaaaggaaa     1980
tcagcaaaat tagggttctt taataagtta taaaactcat ttatatacaa aattaattac     2040
attacaaaag gtgggaatgt ggatttagac atacaaccta taataattaa ttaaaaacaa     2100
tacacatgtt tcacaatttg agataattaa atttttaatcc ccatttgata agtaatgatt     2160
ttatcttata aattagtttg ttaggtctat actttatttg tttattttatt tattcttact     2220 cttttttaat tatattttta cttatatccc aagcttcatt aacgattaat ctaagtttga     2280
aatgattaat tacaaaatag tagtctattt tgatctatca cggactattg tgggtatttt     2340
ataatatttt gttatatttt ataaatattt ttagttcatt ttgctatatt tgaaaataac     2400
catatattat ttatattttta ttttttctaga aaatatttttc cataaactca agttctatat     2460
ttaaaatata tattcaaaag tttcctatta caaccctaag ttgaatactt atagaattgt     2520
```

```
aataaaataa gataattaac taaataagtc taattaaaca ctaataattt gaattaacaa    2580
cactaaacaa atattgtcaa caaaacttag ttcaattgac atctatatga agaatcgagt    2640
tccaaatctt cacacctgaa cattaacaaa attatatagt aattatctta attaattctc    2700
ctcatcgata aagtgaatat ctaattaaaa atttaaagtc aaaagtgtga atttcttgaa    2760
atatcaaatt aagacaaaat tcaaatcaat ttgaaaacat ataaacaaaa tggtaaatta    2820
gacaaaaaaa aaaaatccta aaaactacat atgaaaaggt tcattaccaa agaagttttt    2880
ccatgaaaaa aaaaaagaaa gaaagagaat aaaatattat atatagttaa taattatgaa    2940 attttttgtat aatcccataa agtttgcaac taaacttaag catatagttt atgacataat    3000
taaggtcact aataatagag aacagttaga gcaaaggtca aacatccact ttattcactc    3060
tctctcaatc atacaaagag atttaattga atctactcat tacaaaatcc ccaatcttat    3120
aataatatta atatcattaa tctcttatat atatatataa tatatataca tatattatct    3180
catgcacatg gattttcatg atcttcaaac cccacgtcgt tgattttcca taaaacctat    3240
atattccact aatcatttat attcattttt ttttttgggt ctaattttaa actatatgtt    3300
ttaaaactcc atagtttgat caattcaaaa aaaaaaaaaa aaaaaagtga gttatacaat    3360
ttttaaaatt tttaggacat aatcttgaca agtatcttta tctctcctac atgaaagagg    3420
gagcataaga ttagcttgac attgtctaaa attggaagtg tatatatata tatatatata    3480
tctataaatt tagaaattaa aataatgggg ttttttcatg aaatatatat taatagcttg    3540
attaaggaag gtttagaggg tgattaaagt gcaataatat tgttgattaa ttgtttttt    3600 tttcttatgt gtatcttagt ttcaaggact catgtttttt ttttcttttt tcttttttggt    3660 cccatggaag agaactttt ttcaattata ggatttgggt ttttagtttt tgggaattat    3720
tgaaaagtta aatttctgt tgctaatgat gggaaaatta tgaaaaatta tatatgcatg    3780
ggttggtggg gtcataagat ctcaagaag cttttatttt gtcattattt ttctttagaa    3840
aatcagaatc ttaatctttt tttttttaca cattggtatt ttggtcccct ctcgtccaac    3900
ccaaatttaa aaaagatcaa aaagaaaaa aaaaaaaaa agaaacagaa acctaatctt    3960
aaatcaattt ccactatgca atccttaatt gtcatgttga tataaaaaaa aatagtaacg    4020
aggcaggaga ttgaaccata aaacttagct ttgtggttat taatacactt agatgatgct    4080
aattgagtta aactcttgat tgacaattaa aagaaaagtt aaatcattag ttaaataatt    4140
aaagtttaat gatcataagt taatatttga tgttgggtat taataaagga gatgcatttg    4200
actaaaaaaa tgattaggta gagactaggg taattaataa ccaatattaa taaagtatgg    4260
ttatggggga attcatgaca aactcaagag gggatgttca tttgggtctt aatgaagtgt    4320
aggaattcaa ataatttaaa aagttattaa taattattat gattttatta ttattatttc    4380
atttgggtct acataagtat aaagaattga ttaaagaggt tgattatgca gaaagaaggg    4440
tgattagaga agtacaatta tgaagggatt tggataaac acataggaac gaatgatttt    4500 cattggggc cttaacaaat aatattcaat tttaaaaaaa ttgactattt gcaattaggt    4560
cttgatcatg aagatcctcg agataaatta tagtttttc ttttttttctt cgcatatgaa    4620 tttgttcgat ataacgaatt ttccgacata tcttacgtac actgataaga tattgtctgc    4680
ttaggatcta tacttgtgat ttattctatt atctaatcaa tgtgagattt tggtctcatt    4740
cctaacaatt ctctgctaat taattgaaca aaggacgatc actgaggctc cattcaaata    4800
ggaactctta tatctaggtt aattactatg ctacattaga acatatcacc tatctgatag    4860
agttcaaaca catatcacac catgagtact actttttgag gctaagctcc actacatctt    4920
```

```
tgtttgacac ccaaatactc tatctacacg actaggttag gagcataaac tttgatacca      4980
tctctttgag acataaactc ccgtcacttt attttttcatt tcattgatct aaaacgtctt     5040
ataccaatag agatagttgt tttcacatat atatacttat attatcctat tgcctagtga     5100
atctttatac aaagcaacat actttaattt tgattaaaca aagagtgatt acacatggag     5160
atcatagcct aattaaataa ttaaagtata attataggga gggattttga gagaaatgta     5220
attcaacaag gattttgcat aagggtctta gataaggaac taaacaacta gaaaaaaaaa     5280
tataatatat atatatataa aagggaaatg aaatcaaaga aagcatccat tctccatata     5340
tataaaaata catatatata tatggggaag agagaagaga ttacaaaact aatttaataa     5400
taaggtagtt gagggggcaa aaagcaaaat acaagagatt ttgatttttg agagaagccc    5460
tttttagcaa aaaaaataaa atagattaat ataacacaca aacacacacc tactcctttt     5520
cttcaaccac cagattcgat tttgcctctc tctctctctc tctctctctc tctctctgtg    5580
gatcttaaac cccaattcaa aatatgatga caaattatta attattattc ctccaaaaat    5640
attttcccta ttaaaaaaaa taccaagaga gagaaaattc aatgattgtt ttttctcttt     5700
tacattattt ttcttttaaa gaaaaaaact tgctataaat agaggtgccc attgtaagag    5760
caacattcaa ttcaacaaat cttcagttca atttctctct ttttggctct caaaagggga    5820
aagaaaaaaa aatcattatt attattattt cattttcttt ctttccctta aatttgagct     5880
gaaggaaaaa aaaaaaaaa aaatcaatgg cgattgagat tgatattgag caaaatccaa    5940
cggttgaact ttcgcgaatc ggaacatcag aaacacacgg cgaagattcg ccgtattttg    6000
ctggctggaa agcgtatgat gaagatccct ataatgaatc aacaaatcct tctggtgtta    6060
ttcaaatggg cttagctgaa aatcaagtaa gaatatataa ctttttttttg ttttgttttg    6120 ctttgtaagg agattgggtt ttttttttta attgggtttg tgttggaatt tatgaaacag    6180
gtgtcatttg acttattgga ggaatatttg gaggaaaatt gtgagggaga agggaattat    6240
ttaaattctg ggtttagaga aaatgcttta tttcaagact atcatggtct tttctcattt     6300
agaagtgcaa tgggaagttt tatgaagag attagaggtg gaaagagcaaa atttgaccca    6360 aatcgagttg ttttaactgc tggtgccact gctgccaatg agcttctcac tttcattctt     6420
gcaaatcctg gcgatgcttt gcttgtcccc actccttact atcctgggta agtttatcat    6480
cacctctacg ttttcgtatt tcatttcaaa aaccactctt tactgtaatt actataccct     6540
cagacattaa aattttaact ttcaaactat tcttaaagta tgagtttgag ggtatttcat    6600
atggggtttt taaatgtaaa tttatttaca tttttccact acttaagtgt cctatatttc    6660
tactaatttc ttcttgtgtt gtactcatat tttctatcgt ggggtggact acgtattttt     6720
acgagactat tcgtataaca tacgaatgag tgcttttttaa accaaattct tcaaaatcca   6780
agtttaattt tggaaactag aaaatgggta gttttttaaa atgttaccaa acgtgatctt    6840
tatccttaca atcaaacatt accaaggata attgcaacta ccgttagact ttatgagtgc    6900
ttttttttcc aactgttcta tatttttaca acattttgag ttgtattcat catttctgtt     6960
aaagatattt atatgtaact aagtattttt ataagacact gttggtataa tttcatgcac    7020
taataatata gttctttttt ccagatttga cagagatttg agatgcagaa caggagtgaa    7080
aattgtacca attcattgtg acagttcaaa caattttcaa ataactccaa aagcattaga    7140
agaagcttat aattcagcaa tggaaatgaa aatcaaagta agaggagttt taatcacaaa    7200
tccatcaaat ccactcggag caacgatcca acgctccaca atcgaagaca ttctagattt     7260
cgttacacgc aaaaacatcc acctcgtatc cgacgaaatc tattccggtt ccgttttctc     7320
```

```
ctccgccgag ttcacaagcg tcgctgaggt tttggaatcc cgcagctaca aaaacgccga   7380
acgtgtccac atcgtttaca gcctctccaa agatctcggc cttcccgggt ttagaatcgg   7440
cacgatctac tcatacaacg ataaagtcgt cacaaccgct cgccggatgt ctagctttac   7500
gcttatctct tcacaaacgc aacgattttt agcgtccatg ttgtcgaacc ggaagtttac   7560
ggagaaatat attaaaatga accgggacag gctcaagaaa cggtatgaaa tgattattga   7620
agggctgcga accgccggga ttgaatgttt ggaagggaat gccggtttgt tttgttggat   7680
gaatttgagc ccgttgttga agataaaaaa accaaagaa ggtgagattg agatatggaa   7740
gaggattttg aaggaagtga aattgaatat ttcgcccggt tcgtcgtgtc attgctctga   7800
acccggttgg ttcagggttt gttttgctaa tatgagtgaa aagactctgc atgttgccct   7860
tgatagaata cgtcggttca tggaacggat gaagaaggaa aacgaagcta attaaatata   7920
tatctatata taaatatatg aaaagaaaaa aaacatatgt agcttatttt atttattt t   7980 tttttacaat ggttgtgaga aaaagaaaa aagaaaaaaa aagaaaaaaa aagccattgt   8040
gattcttttg tgtggacact gcccaatatt tgttagaaat ttggggtttt ttgtcttcat   8100
ttatacgtca tattttgatg atttaaactg aggaaaaaga aaaagaaatc cttgtttttct   8160 tgcttttagc aaagcaagtt ttatttctca gttttatata tatatatata taaagtttct   8220
atttgtattg tcatttttat gtgatatgga atataattag tataattcgt tcttgcaatt   8280
aattacctcg aaaataaacg aaatacaaga aaaagaaaaa aaaaatctca tggagtattt   8340
tagggacaag tgtcaactca gggagagaga aaaaaatatg gtttaaattt aatagtattg   8400
gttattttca taacatgctc taaaaaggaa tataactaat aatttgactt taattaagaa   8460
aagaaaagct aataatatat aattaaaatc actttttagca acgaataaca ctttgccgac   8520 tgtgtaatt aaccacctaa ctatccatct gacgtggaat gcaagtaatt aattaattga   8580 tttttcgtt ttcaaatttt ggtcaacttg attcttggta ctaatttaat gtttccatct   8640
gtcagaaagc tacaacgttt ttcctccttc tttctttttt ttaagaatta ttttaaaaag   8700
tcaatacggt gctataatta gattttatt tttcctcttt tttagtgtat atatatattt   8760
atataagtag agattaggaa ctaattgatt gaaaattaaa tatgctgtga cgctcaaaag   8820
atattaatcc cgcgttggtt ttatgtattt aaaaaatgta ttttttcttt tttgatattt   8880
ttaaataata aaatatttaa attatttaca aaatataaca aaatttgctc gtttacattt   8940
ttattttgtg aaggacttat gcgatgtggt tcgatctaga attcttgtat tttcaaaata   9000
gatggagctt cttttttggat gaattctctc taggcttctg aagtcaaaaa ttttcaaccc   9060
aagaaaaaac tagagtttcc ttgtggtatg aggtgtatga aattgactca ttgactcaat   9120
tacatggact tttatcatat ttaactcagc taaattaagt ttattttttg gaattaatct   9180
aagtaaataa tatttaattg aaccaaaata tttaatttga tcagtcataa taaagacatg   9240
tgacatcatt ggaatcagtc aatttgtgtt taaatttaat ttgggataca tgtcaacttt   9300
tagttaatct caaatgcaat ttgtgattag ttacaaaatt tcttattcaa catacttcaa   9360
atctaaattt ggtaaattat gttttttta aagaaattag atcaacacaa aaatataata   9420
tgttttgtga aaatgaaaat tttggttaa tgggaggaga caaatttgaa cgacaaattt   9480
tcttagtaac ttacgatatg atcactaact aatttattat aggttggggg tttgaacctc   9540
tctcaacttt gtgctcatta tataatatat ctttaaaaga ccgaccttgc attaatgttg   9600
ttggttagtc tagtggtaga atcgtcattc tctagctctc tctaaattgt tccagcttca   9660
gtttttatat acttttttat attatttta ctgaactata aaaaattact gtcgacaaaa   9720
```

```
tttatgcttt tatcacttaa cataataatt gaactatgtt tgctttgttt tttcttttt     9780
aacgtatact atctcaaagt tttggataat gtacgtgttt gaaattttgt aacaaacaag    9840
gatacataaa tacgtaattg ttgttaatta tttcaaaatg taaatagatg atatgatgta    9900
ggggttgcta atattattgt ctaattattt ttgtaaagaa taaaataaaa taaaaatcca    9960
tatgatgcct aaggacgtgt ttagtattca atatggcgat tattatgtct tttttttcaaa   10020
tggattactt tttggatgat atgatatctt ttattttaat taaaacttttt tgatgacttt   10080
taaaatttaa agggcataaa atatagcttt cttttgtaca tatatatggt tgtgcttgga   10140
ttttgtatct gcttgtcttt gtcccgagtt tctcgtcggt ttgaccttcg atctactttt   10200
tttgatatat atgttccaat atcgatttct aagctaacat atgtaaaaga tgattgcact   10260
cgtgtggtgc tgagactatc acacttgata cttgatataa gattgtatta ttcatctgaa   10320
ccaataaaaa ttaagatgga tattactcac tcttctcttt taggatcatc aaacaaggct   10380
ctttttttga caatcacctg aagtcacgag taactctaca gtgttatagt tgtttatagt   10440
atttgagact ggaaatatca aattcagcca attcaattaa attttataat tgatatacat   10500
tcatatgctc gaaagttgg cttccaaccg tccaacgctc taactttggg acatgtgtta    10560
caaaacacat aggtttaaaa aaatacctaa aaacataaaa aatacaactt tgatcatcct    10620
ttagttcaat tttattccca atttgatact tttgaattcc ctaactagag aattgtaatt    10680
gtgattgaac gttttatag tcaaaattg gatttgatag cttataggac cccatgtgcc     10740
aaacaaaata aaaattgcat atatatatat agagagagag ggggagtttt atatttaaa    10800
aaacaaaatt agaaaaggc aattaatttt gttctttaaa cgacatggtt tctcacgtgt    10860
taaacgtcat tgttatcaac tgcgtcttgt cgctgaccaa ttcattgaca gcacagcaag   10920
caaaaagaa aaagaaaaa aaaagtcaa aaagttaatg tggttaaaga aagcgctttt     10980
tgtgataact caaaaaaaca aaccaaccaa tggaagccct ccaggtcact ctcatgtggc   11040
tcccgtctcc acgtcatcaa tgaacacgga cgtgtttaca gctcaacaaa caacaactat   11100
tcctctgacg tggcaatttc ttattaatga atttccaact ctgccctcct attacatttt   11160
cttaaggtcg gtgaatgccg tacaatggaa gctcctagac atactttcta gttgtgatat   11220
atatatatat atattattca tccatcatat attaaactcc aatgtatgtt tgtggatttt   11280
acaaagtta atattttg gtagatgttg agatttcttt ttttttccaat gtctagtctt     11340
tttccaagtt tggagaaagt tttttatgat gttgggagtt atttaatttc ctagtggggc   11400
cacgtagtta aataaatata ggttaaattt tacgaaatat ccatatatcg cgtgtgtggt   11460
atgatttcag ttacgtcact attttgaaaa catagttttc gtgttcttat taatgcttat   11520
agttgtaaat aacataatta aaagtatcat ttgttaaaat tgatgtcaca ccgtatgtac   11580
ataatttatt tattgattga tgttataagg ggcgttggag atatcgttgg aaaaaaatga   11640
tttgtaagga tgatcttaat tttctataat tgactcacgt atattatatt gtatacgttt   11700
ttcaaaattt acacaccaat catctcactt tcgttttcat ttttcatttt agtggaaaac   11760
aattcaataa aaaaaaattc tgacaacttt ttaaaattta aggcacagtt gaatcaatcc   11820
aaccgttcaa gatttaaaga agaaaaaaac taatttggtt gctccacttt ttgttttttgt  11880
tcgttttggt ccattaattc taaaaatgtt taatttatttt gttatacttt caaatcttca   11940
caactttacc gtattgatcc cttaaaaatg aagtaaaaac aataatgaac gaactaagac    12000
aatcaccatt tgaaagttta aggaccaaat gaaccaaagt taaagtata gaaacaaaaa     12060
taaacatcgc taaataaacc aaataaaact agaattactt aattgaaaca aataatatg    12120
```

-continued

```
aaatggatca aatctttaga ctttagtgta tgggaaagtt ctatgaaaat gaccaccgac   12180
tatcgagaga ccaattttgg ggccaagtca atgattggta atttcaacct acatttatga   12240
tgtatgacaa tgacaatagc ttaggtcact ttgaaaatga ctataagatt ttctagttag   12300
agatatacac ttgatattag acttggtcgt tgtaataaaa actatgtgtc acggatgata   12360
tatgctaagt acatgttttta gtctttaatg tttgcgtata tttctttacg taatttaatc   12420
ttcgttaatt atattttta aactatgttt taatctttta attcttttgt tgtgaaattg   12480
acaaataaag agaaacacga caatgtagat ggtaaacaat gaagtttgtg tagtttattg   12540
acaatatgtt ggcaatgttt acgagtagag agataattgt tcaaattaca gaacaatagg   12600
tgacaatacg tgagtttttg ttttaattta cttttgaaac tttattttga ttttcaaaac   12660
ttaaagaagt tgatactatt attgttttga gctatgaaga tgtgtgatcg aacctttcac   12720
acgtttagaa tgaaagagca tgtcaattaa ttttgagcta aacttgttta aaaaaattga   12780
ccttttgtct ttgttttaag ttttaacaaa ttaatgatgt cattgcgtaa ttttaagtca   12840
gttaggtatg aaaagccacc atcgaagaaa gaaaatttca agaagaaaag caatgtagta   12900
aatcacaaat aattgttttt ctttcccata ggttataact ataaaaaaaa aacttctttt   12960
ttagtataat aacggtaaag aaggatgatc aaaccttcta actcagtcaa ttgcaaatat   13020
gataaattca ctttgacaaa ctaaaataaa tttgaagatt tatgaaacaa aatgtacatt   13080
ttaaaagttt atattttcac acaatgttag cttcctttta aaaaaaaatt aaattttaaa   13140
agttcagaga acaaaacata catttcaact ttgctaactt caatatagaa cttatataaa   13200
atcgtgccac atagggttca aaagaactat aggattttaa aatgaaaaca tatattttaa   13260
ttgagtttta gaactaagtt aatatatttta ttaataaga ataacacttc agtaaaatta   13320
agaacaacac agacatagtt caataacata aaactagtac cttttacatc aatattgaa   13380
```

<210> SEQ ID NO 2
<211> LENGTH: 11137
<212> TYPE: DNA
<213> ORGANISM: Cucumis melo

<400> SEQUENCE: 2

```
tagtctatttt tgatctatca cgaactattg taggtatttt ataatatttt gttatatttt     60
ataaatattt ttagttcatt ttgctatatt taaaaataac catatattat ttatatttta   120
tttttctaaa aaatattttc cataaactca agttctatat ttaaaatata tattcaaaac   180
tttcttatta caaccctaag ttgaatactt atagaattgt aataaaataa gataattaac   240
taaataagtc taattaaaca ttaataattt gaattaacaa cactaaacaa atattgtcaa   300
caaaacttag ttcaattgac atctatatga agaatcgact tccaaatctt cgcacctgaa   360
cattaacaaa attatatagt aattatctta attaattatc ctcatcgata aagtgaatat   420
ctaattaaaa atttaaagtc aaagtgtga atttcttgaa atatcaaatt aagacaaaat   480
tcaaatctct ttagagtaaa attatagaat ttgaaaacat ataaacgaaa aatggtaaat   540
tagacaaaaa aaaaatatat ttttttctaaa aactacatat gaaaaggttc attaccaaag   600 aagttttttcc atgaaaaaaa aaagaaagaa agaaagaaag agaataaaat attatatata   660
gttaataatt atgaaatttt tgtataatcc cataaagttt gcaactaaac ttaagcatat   720
agtttatgac ataattaagg tcactaataa tagagaacag ttagagcaaa ggtcaaacat   780
ccactttatt cactctctct caatcataca aagagattta attgaatcta ctcattacaa   840
aatccccaat cttataataa tattaatatc attaatctct tatatatata taatatatat   900
```

```
atacatatat tatctcatgc acatggattt tcatgatctt caaaccccac gtcgttgatt      960
ttccataaaa cctatatatt ccactaatca tttatattca ttttttttt tgggtctaat      1020 tttaaactat atgttttaaa actccatagt ttgatcaatt caaaaaaaaa aaaaaaaaa      1080 aaagtgagtt atacaatttt taaaattttt aggacataat cttgacaagt atctttatct      1140
ctcctacatg aaagagggag cataagatta gcttgacatt gtctaaaatt ggaagtgtat      1200
atatatatat atatatatct ataaatttag aaattaaaat aatggggttt ttcatgaaa       1260 tatatattaa tagcttaatt aaggaaggtt tagagggtga ttaaagtgca ataatattgt      1320
tgattaattg ttttttttc ttatgtgtat cttagtttca aggactcatg tttttttttt       1380
cttttttctt tttggtccca tggaagagaa ctttttttca attataggat tgggttttt       1440 agttttggg aattattgaa aagttataat ttctgttgct aatgatggga aaattatgaa       1500
aaattatata tgcatgggtt ggtggggtca taagatctca aagaagcttt tattttgtca     1560 ttattttct ttagaaaatc agaatcttaa tcttttttt ttacacattg gtattttggt        1620
cccctctcgt ccaacccaaa tttaaaaaag atcaaaaaag aaaaagaaa aaaaaaaaa        1680 gaagaagaag aaacctaatc ttaaattaat ttccactatg caatccttaa ttgtcatgtt      1740
gatataaaaa aaaatagtaa cgaggtagga gattcaacca taaaacttag ctttgtggtt     1800
attaatacac ttagatgatg ctaattgagt taaactcttg attgacaatt aaaagaaaag     1860
ttaaatcatt agttaaataa ttaaagttta atgatcataa gttaatattt gatgttgggt     1920
attaataaag gagatgcatt tgactaaaaa aatgattagg tagagactag ggtaattaat     1980
aacaaatatt aataaagtat ggttatgggg gaattcatga caaactcaag aggggatgtt     2040
catttgggtc ttaatgaagt gtaggaattc aaataattta aaaagttatt aataattatt     2100
atgattttat tattattatt tcatttgggt ctacataagt ataaagaatt gattaaagag     2160
gttgattatg cagaaagaag ggtgattaga gaagtacaat tatgaaggga ttttggataa     2220
acacatagga acgaatgatt ttcattgggg gccttaacaa ataatattca attttaaaa      2280 aattgactat ttgcaattag gtcttgatca tgaagatcct cgagataaat tatagttttt     2340
tcttgttttc ttcgcatatg aatttgttcg atataacgaa ttttccgaca tatcttacgt     2400
acactgataa gatattgtct gcttaagatc tatacttgtg atttattcta ttatctaatc     2460
aatgtgagat tttggtctca ttcctaacaa ttctctgcta attaattgaa caaggacga     2520 tcactgaggc tccattcaaa taggaactct tatatctagg ttaattacta tgctacatta     2580
gaacatatca cctatctgat agagttcaaa cacatatcac accatgagta ctactttcg     2640 aggctaagct ccactacatc tttgtttgac acccaaatac tctatctaca cgactaggtt     2700
aggagcataa acttttgatac catctctttg agacataaac tcccgtcact ttatttttca    2760
tttcactgat ctaaaacgtc ttataccaat agagatagtt gttttcacat atatatactt     2820
atattatcct attacctagt gaatctttct gcaaagcaca tacttttaatt ttgattaaac    2880 aaaaagtgat tacacatgga tatcatagcc taattaaata attaaagtat aattatgggg     2940
ggggggggat tttgagagaa atgtaattca acaaggattt tgcataaggg tcttagataa     3000
ggaactaaac aactagaaaa aaaatataat atatatatat ataaaaaagg gaatgaaat      3060 caaagaaagc atccattctc catatatata aaaatacata tatatatatg gggaagagag     3120
aagagattac aaaactaatt taataataag gtagttgagg gggcaaaaag caaaatacaa     3180 gagatttttga ttttgagag aagccctttt tagcaaaaaa aataaaatag attaatataa     3240
cacacaaaca cacacctact cctttttcttc aaccaccaga ttcgattttg cctctctctc    3300
```

```
tctctctctc tctctctctc tctctctgga tcttaaaccc caattcaaaa tatgatgaca    3360
aattattaat tattattcct ccaaaaatat tttccctatt aaaaaaaata ccaagagaga    3420
gaaaattcaa tgattgtttt ttctctttta cattattttt tttttaaaga aaaaaacttg    3480
ctataaatag aggtgcccat tgtaagagca acattcaatt caacaaatct tcagttcaat    3540
ttctctcttt ttggctctca aaagggaaa gaaaaaaaaa tcattattat tattatttca    3600 ttttcttttct ttcccttaaa tttgagctga aggaaaaaaa aaaaaaatca atggcgattg    3660
agattgatat tgagcaaaat ccaacggttg aactttcgcg aatcggaaca tcagaaacac    3720
acggcgaaga ttcgccgtat tttgctggct ggaaagcgta tgatgaagat ccttataatg    3780
aatcaacaaa tccttctggt gttattcaaa tgggcttagt tgaaaatcaa gtaagaatat    3840
ataacttttt tttgttttgt tttgctttgt aaggagattg gggtttttt ttaattgggt    3900 ttgtgttgga atttatgaaa caggtgtcat ttgacttatt ggaggaatat ttggaggaaa    3960
attgtgaggg agaagggaat tatttaaatt ctgggtttag agaaaatgct ttatttcaag    4020
actatcatgg tcttttctca tttagaagtg caatgggaag tttttatggaa gagattagag    4080 gtggaagagc aaaatttgac ccaaatcgag ttgttttaac tgctggtgcc actgctgcca    4140
atgagcttct cactttcatt cttgcaaatc ctggcgatgc tttgcttgtc cccactcctt    4200
actatcctgg gtaagtttat catcacctct acgttttcgt atttcatttc aaaaaccact    4260
ctttactgta attactatac cctcagacat taaaatttta actttcaaac tattcttaaa    4320
gtatgagttt gagggtattt catatggggt ttttaaatgt aaatttattt acatttttcc    4380
actacttaag tgtcctatat ttctactcat ttcttcttgt gttgtactca tattttctat    4440
cgtggggtgg actacgtatt tttacgagac tattcgtata acatacgaat gagtgcttttt    4500 taaaccaaat tcttcaaaat ccaagtttaa ttttggaaac tagaaaatgg gtagtttttt    4560
aaaatgttac caaacgtgat ctttatcctt acaatcaaac attatcaagg ataattgcaa    4620
ctatcattag actttatgag tgcttttttt ttccaactgt tctatatttt tacaacattt    4680
tgagttatat tcatcacttc tgttaaagat atttatatgt aactaagtat ttttataaga    4740
cactgttggt ataatttcat gcactaataa tatagtttct ttttccagat ttgacagaga    4800
tttgagatgg agaacaggag tgaaaattgt accaattcat tgtgacagtt caaacaattt    4860
tcaaataact ccaaaagcat tagaagaagc ttataattca gcaatggaaa tgaaaatcaa    4920
agtaagagga gttttaatca caaatccatc aaatccactc ggagcaacga tccaacgctc    4980
cacaatcgaa gacattctag atttcgttac acgcaaaaac atccacctcg tatccgacga    5040
aatctattcc ggttccgttt tctcctccgc cgagttcaca agcgtcgctg aggttttgga    5100
atcccgcagc tacaaaaacg ccgaacgtgt ccacatcgtt tacagcctct ccaaagatct    5160
cggccttccc gggtttagaa tcggcacgat ctactcatac aacgataaag tcgtcacaac    5220
cgctcgccgg atgtctagct ttacgcttat ctcttcacaa acgcaacgat ttttagcgtc    5280
catgttgtcg aaccggaagt ttacggagaa atatattaaa atgaaccggg acaggctcaa    5340
gaaacggtat gaaatgatta ttgaagggct gcgaaccgct gggattgaat gtttggaagg    5400
gaatgccggt ttgttttgtt ggatgaattt gagcccgttg ttgaaagata aaaaaaccaa    5460
agaaggtgag attgagatat ggaagaggat tttgaaggaa gtgaaattga atatttcgcc    5520
cggttcgtcg tgtcattgct ctgaacccgg ttggttcagg gtttgttttg ctaatatgag    5580
tgaaaagact ctgcatgttg ccccttgatag aatacgtcgg ttcatggaac ggatgaagaa    5640
ggaaaacgaa gctaattaaa tatatatata tatatatata aatatatgaa aagaaaaaaa    5700
```

-continued

```
acatatgtag cttattttat tttattttttt ttttacaatg gttgtgagaa aaaagaaaaa      5760
agaaaaaaga aaaaaaaaaa gaaaaaaaag ccattgtgat tcttttgtgt ggacactgcc      5820
caatatttgt tagaaatttg gggttttttg tcttcattta tacgtcatat tttgatgatt      5880
taaactgagg aaaaagaaaa agaaatcctt gttttcttgc ttttagcaaa gcaagtttta      5940
tttctcagtt ttatatatat atataaagtt tctatttgta ttgtcatttt tatgtgatat      6000
ggaatataat tagtataatt cgttcttgca attaattacc tcgaaaataa acgaaataca      6060
agaaaaagaa aaaaaaaatc tcatggagta ttttagggac aagtgtcaac tcagggagag      6120
agaaaaaaat atggtttaaa tttaatagta ttggttattt tcataacatg ctctaaaaag      6180
gaatataact aataatttga ctttaattaa gaaaagaaaa gctaataata tataattaaa      6240
atcactttta gcaacgaata acactttgcc gacttgtgta attaaccacc taactatcca      6300
tctgacgtgg aatgcaagta attaattaat tgattttttc gttttcaaat tttggtcaac      6360
ttgattcttg gtactaattt aatgtttcca tctgtcagaa agctacaacg ttttttcctcc     6420 ttctttcttt tttttaagaa ttattttaaa aagtcaatac ggtgctataa ttagattttt      6480 attttttcctc tttttttagtg tatatatata tttatataag tagagattag gaactaattg    6540
attgaaaatt aaatatgctg tgacgctcaa aagatattaa tcccgcgttg gttttatgta     6600
tttaaaaaat gtattttttc tttttttgata ttttttaaata ataaaatatt taaattattt   6660
acaaaatata acaaaatttg ctcgtttaca tttttatttt gtgaaggact tatgcgatgt      6720
ggttcgatct agaattcttg tattttcaaa atagatggag cttcttttttg gatgaattct    6780 ctctaggctt ctgaagtcaa aaattttcaa cccaagaaaa aactagagtt tccttgtggt     6840
atgaggtgta tgaaattgac tcattgactc aattacatgg acttttatca tatttaactc     6900
agctaaatta agtttatttt ttggaattaa tctaagtaaa taatatttaa ttgaaccaaa     6960
atatttaatt tgatcagtca taataaagac atgtgacatc attggaatca gtcaatttgt    7020
gtttaaattt aatttgggat acatgtcaac ttttagttaa tctcaaatgc aatttgtgat     7080
tagttacaaa atttcttatt caacatactt caaatctaaa tttggtaaat tatgtttttt     7140
ttaaagaaat tagatcaaca caaaaatata atatgttttg tgaaaatgaa aattttggtt    7200
taatgggagg agacaaattt gaacgacaaa ttttcttagt aacttacgat atgatcacta     7260
actaatttat tctaggttgg gggtttgaac ctctctcaac tttgtgctca ttatataata     7320
tatctttaaa agaccgacct tgcattaatg ttgttggtta gtctagtggt agaatcgtca    7380
ttctctagct ctctctaaat tgttccagct tcagttttta tatactttttt tatattattt    7440 ttactgaact ataaaaaatt actgtcgaca aaatttatgc ttttatcact taacataata    7500
attgaactat gtttgctttg ttttttcttt tttaacgtat actatctcaa agttttggat    7560
aatgtacgtg tttgaaattt tgtaacaaac aaggatacat aaatacgtaa ttgttgttaa     7620
ttatttcaaa atgtaaatag atgatatgat gtaggggttg ctaatattat tgtctaatta    7680
tttttgtaaa gaataaaata aaataaaaat ccatatgatg cctaaggacg tgtttagtat    7740
tcaatatggc gattattatg tcttttttttc aaatggatta cttttttggat gatatgatat    7800 cttttattt aattaaaact ttttgatggc ttttaaaatt taaagggcat aaaatatagc    7860
tttcttttgt acatatatat ggttgtgctt ggattttgta tctgcctgtc tttgtcccga    7920
gtttctcgtc ggtttgacct ccgatctact tttcttgata tatatgttcc aatatcgatt    7980
tctaagctaa catatgtaag agatgattgc actcgtgtgg tgtcgagact atcacacttg    8040
atacttgata taagattgta ttattcatct gaaccaataa aaattaagat ggatattact    8100
```

-continued

```
cactcttctc ttttaggatc atcaaacaat gctctttttt tgacaatcac ctgaagtcat    8160
gagtaactct acagtgttat agttgtttat agtatttgag actagaaata acaaattcag    8220
ccaattcaat taaattttat aattgatata cattcatatg ctcgaaaagt tggcttccaa    8280
ccgtccaacg ccctaacttt gggacatgtg ttacaaaaca cataggttta aaaaaatacc    8340
taaaaacata aaaaaaaata caattttgat catcctttag ttcaattta ttcccaattt     8400
gatactttg aattccctaa ctagagaatt gtaattgtga ttgaacgttt ttatagtcaa     8460
aatttggatt tgatagctta tagaaccccca tgtgccaaac aaaataaaaa ttgcatacat   8520
atatatatat atatatatat atatatatat atatatatat atatatatat atatagaggg    8580
agttttatat tttcaaaaac aaaattagaa aaaggcaatt aattttgttc tttaaacgac    8640
atggtttctc acgtgttaaa cgtcattgtt atcaactgcg tcttgtcgct gaccaattca    8700
ttgacagcac agcaagcaaa aagaaaaaa aaaaaaaaa aagtcaaaaa gttaatgtgg      8760
ttaaagaaag cgcttttttgt gataactcaa aaaaacaaac caaccaatgg aagccctcca   8820
ggtcactctc atgtggctcc cgtctccacg tcatcaatga acacggacgt gtttacagct    8880
caacaaacaa caaccattcc tctgacgtgg caatttctta ttaatgaatt tccaactctg    8940
ccctcctatt acattttctt aaggtcggtg aatgccgtac aatggaagct cctagacata    9000
cttctagtt gtgatatata tatatatata tatatattat tcatccatca tatattaaac     9060
tccaatgtat gtttgtggat tttacaaaag ttaatattat ttggtagatg ttgagatttc    9120
tttttttcc aatgtctagt cttttttccaa gtttggagaa agtttttttat gatgttggga   9180
gttatttaat ttcctagtgg ggccacgtag ttaaataaat ataggttaaa ttttacgaaa    9240
tatccatata tcgcgtgtgt ggtatgattt cagttacgtc actattttga aaacatagtt    9300
ttcgtgttct tattaatgct tatagttgta aataacataa ttaaaagtat catttgttaa    9360
aattgatgtc acaccgtatg tacataattt atttattgat tgatgttata aggggcgttg    9420
gagatatcgt tggaaaaaaa tgatttgtaa ggatgatctt aattttctat aattgactca    9480
cgtatattat attgtatacg ttttttcaaaa tttacacacc aatcatctca ctttcgtttt    9540
cattttcat tttagtggaa aacaattcaa aaaaaaaaaa aattctgaca acttttttaaa    9600
atttaaggca cagttgaatc aatccaaccg ttcaagattt aaagaagaaa aaaactaatt    9660
tggttgctcc acttttttgtt tttgttcgtt ttggtccatt aattctaaaa atgtttaatt    9720
tatttgttat actttcaaat cttcacaact ttaccgtatt gatcccttaa aaatgaagta    9780
agtcaatcac catttgaaag tttaaggacc aaatgaacca agttaaaag tataaaaaca     9840
aaaataaaca tcgctaaata aaccaaataa aactagaatt acttaattga aacaaaataa    9900
tatgaaatgg atcaaatctt tagactttag tgtatgggaa agttctatga aaatgaccac    9960
cgactatcga gagaccaatt tggggccaa gtcaatgatt ggtaatttca acctacatttt    10020
atgatgtatg acaatgacaa tagcttaggt cactttgaaa atgactataa gattttctag    10080
ttagagatat acacttgata ttagacttgg tcgttgtaat aaaaactatg tgtcacggat    10140
gatatatgct aagtacatgt tttagtcttt aatgtttgcg tatatttctt tacgtaattt    10200
aatcttcgtt aattatattt tttaaactat gttttaatct tttaattctt ttgttgtgaa    10260
attgatacaa ataaagaggt ttctctttat tgacaatatg ttgcgtagtt tattgacaat    10320
atgttggcaa tgtttacgag tagagagata attgttcaaa ttacagaaca ataggtgaca    10380
atacgtgagt tttgttttta atttagtttt gaaactttat tttgattttc aaaacttaaa    10440
gaagttgata ctattattgt tttgagctat gaagatgtgt gatcgaacct ttcacacgtt    10500
```

-continued

```
tagaatgaaa gagcatgtca attaattttg agctaaactt gtttaaaaaa attgaccttt   10560
tgtctttgtt ttaagtttta acaaattaat gatgtcattg cgtaatttta agtcagttag   10620
gtatgaaaag ccaccatcga agaaagaaaa tttcaagaag aaaagcaatg tagtaaatca   10680
caaataattg ttttctttc ccataggtta aactataaa aaaaaacttc ttttttagta    10740
taataacggt aaagaaggat gatcaaacct tctaactcag tcaattgcaa atatgataaa   10800
ttcactttga caaactaaaa taaatttgaa gatttatgaa acaaaatgta cattttaaaa   10860
gtttatattt tcacacaatg ttagcttcct tttaaaaaaa atttaaattt taaaagttca   10920
gagaacaaaa catacatttc aactttgcta acttcaatat agaacttata taaaatcgtg   10980
ccacataggg ttcaaaagaa ctataggatt ttaaaatgaa aacatatatt ttaattgagt   11040
tttagaacta agttaatata tttatttata aagaataaca cttcagtaaa attaagaaca   11100
acacagacat agttcaataa cataaaacta gaggatc                           11137
```

<210> SEQ ID NO 3
<211> LENGTH: 445
<212> TYPE: PRT
<213> ORGANISM: Cucumis melo

<400> SEQUENCE: 3

```
Met Ala Ile Glu Ile Asp Ile Glu Gln Asn Pro Thr Val Glu Leu Ser
1               5                   10                  15

Arg Ile Gly Thr Ser Glu Thr His Gly Glu Asp Ser Pro Tyr Phe Ala
            20                  25                  30

Gly Trp Lys Ala Tyr Asp Glu Asp Pro Tyr Asn Glu Ser Thr Asn Pro
        35                  40                  45

Ser Gly Val Ile Gln Met Gly Leu Ala Glu Asn Gln Val Ser Phe Asp
    50                  55                  60

Leu Leu Glu Glu Tyr Leu Glu Glu Asn Cys Glu Gly Glu Gly Asn Tyr
65                  70                  75                  80

Leu Asn Ser Gly Phe Arg Glu Asn Ala Leu Phe Gln Asp Tyr His Gly
                85                  90                  95

Leu Phe Ser Phe Arg Ser Ala Met Gly Ser Phe Met Glu Glu Ile Arg
            100                 105                 110

Gly Gly Arg Ala Lys Phe Asp Pro Asn Arg Val Val Leu Thr Ala Gly
        115                 120                 125

Ala Thr Ala Ala Asn Glu Leu Leu Thr Phe Ile Leu Ala Asn Pro Gly
    130                 135                 140

Asp Ala Leu Leu Val Pro Thr Pro Tyr Tyr Pro Gly Phe Asp Arg Asp
145                 150                 155                 160

Leu Arg Trp Arg Thr Gly Val Lys Ile Val Pro Ile His Cys Asp Ser
                165                 170                 175

Ser Asn Asn Phe Gln Ile Thr Pro Lys Ala Leu Glu Glu Ala Tyr Asn
            180                 185                 190

Ser Ala Met Glu Met Lys Ile Lys Val Arg Gly Val Leu Ile Thr Asn
        195                 200                 205

Pro Ser Asn Pro Leu Gly Ala Thr Ile Gln Arg Ser Thr Ile Glu Asp
    210                 215                 220

Ile Leu Asp Phe Val Thr Arg Lys Asn Ile His Leu Val Ser Asp Glu
225                 230                 235                 240

Ile Tyr Ser Gly Ser Val Phe Ser Ser Ala Glu Phe Thr Ser Val Ala
                245                 250                 255

Glu Val Leu Glu Ser Arg Ser Tyr Lys Asn Ala Glu Arg Val His Ile
            260                 265                 270
```

```
Val Tyr Ser Leu Ser Lys Asp Leu Gly Leu Pro Gly Phe Arg Ile Gly
        275                 280                 285

Thr Ile Tyr Ser Tyr Asn Asp Lys Val Val Thr Thr Ala Arg Arg Met
        290                 295                 300

Ser Ser Phe Thr Leu Ile Ser Ser Gln Thr Gln Arg Phe Leu Ala Ser
305                 310                 315                 320

Met Leu Ser Asn Arg Lys Phe Thr Glu Lys Tyr Ile Lys Met Asn Arg
                325                 330                 335

Asp Arg Leu Lys Lys Arg Tyr Glu Met Ile Ile Glu Gly Leu Arg Thr
                340                 345                 350

Ala Gly Ile Glu Cys Leu Glu Gly Asn Ala Gly Leu Phe Cys Trp Met
                355                 360                 365

Asn Leu Ser Pro Leu Leu Lys Asp Lys Lys Thr Lys Glu Gly Glu Ile
        370                 375                 380

Glu Ile Trp Lys Arg Ile Leu Lys Glu Val Lys Leu Asn Ile Ser Pro
385                 390                 395                 400

Gly Ser Ser Cys His Cys Ser Glu Pro Gly Trp Phe Arg Val Cys Phe
                405                 410                 415

Ala Asn Met Ser Glu Lys Thr Leu His Val Ala Leu Asp Arg Ile Arg
                420                 425                 430

Arg Phe Met Glu Arg Met Lys Lys Glu Asn Glu Ala Asn
                435                 440                 445

<210> SEQ ID NO 4
<211> LENGTH: 18
<212> TYPE: DNA
<213> ORGANISM: Cucumis melo

<400> SEQUENCE: 4
gactgcgtac atgcagca                                                        18

<210> SEQ ID NO 5
<211> LENGTH: 27
<212> TYPE: DNA
<213> ORGANISM: Cucumis melo

<400> SEQUENCE: 5
cgtattttgc tggctggaaa gcgtatg                                              27

<210> SEQ ID NO 6
<211> LENGTH: 27
<212> TYPE: DNA
<213> ORGANISM: Cucumis melo

<400> SEQUENCE: 6
cgatagaaaa tatgagtaca acacaag                                              27

<210> SEQ ID NO 7
<211> LENGTH: 16177
<212> TYPE: DNA
<213> ORGANISM: Cucumis melo

<400> SEQUENCE: 7
ggaaacagct atgaccatga ttacgccaag ctcggaatta accctcacta aagggaacaa         60
aagctggagc tccaccgcgg tggcggggc gctctagcc acagacagct ccgtagcccc         120
cgttctcctt ggagttcttc gggaaatgga tctttcgatt cccgatgatg tctctcttat        180
ctgctttgac gacgccgact ggacatccgc tataacgccg ccattgaccg tgatttcgca        240
acctgtcagg gatctcgcga cggctgccac agaagacctg atcgcccgct aaagggcga         300
```

```
gacttcagcc ccacccaagg aaactcttct cccggcggtt ctcatagagc gcggttccgt    360
aagcggttct tcgcaaggtc gggggttgcat accgaactcg cgaaacgtcg cgactgagc    420 tcccgaggcg cgttgacaag atgccacgaa gggaatggaa gacagccgat attgcaattg    480
tcttcgtgga ctgctttcgg gacgtaaggc gcaagccatc atcaccgccg tcctaaacaa    540
acatacctcc acacaaattt atctacctga ccacaagata tatcctgtca cacgatttat    600
taaacgctgc acttggctag aactagtgga tccgcggccg catgcctgca ggtcgactct    660
agttgattaa ttgtttaggc tttattatat attcatcata agtctttttt gtagccattt    720
aggtttgttt tcgtcgaatt aatcttataa acactatttt tattcgtaaa ttccgttgct    780 ttcttatttta ctttatatca atgctttaaa acatcaatct agttttttaaa aatcaatata    840 tatgtttgca cacccatta ttatcgtatg ttactctatc tattactgac aaacgttatg    900 aaatttttatt atatttgtaa ttatcttttg cagttttgtc atttaaaatc gttttttctta   960 aaagaattat gttgttatttt taaaattttg gctaaagaat cacgtggaga attagatata  1020
tcaaaccttt catctttgag atgaaagatt acatcaatta ctattaacta agcttacttt  1080
gataaattaa aatcatatta aaacaaatag tccgtaaaag aatataattt tgaaaaacta  1140
aacagtcatc aaacaacgcg tgttagcttt taatatatat tatgatatgt taagtgaaaa  1200
taaagttgaa gtgtatgaag ccaaagagaa agtcgttttc acttgttgag ttctaatttc  1260
taggatggtt ctatgtaaag tacttcctct tccaaaattg gaatccaact cactacttat  1320
aaacatcatt tattcgtcat cttaattaca ataccaactc ttattttttgt ctcatctatc  1380 atcacactca ctaattaaca ttaccattat cttatatcat tttatgaact cattatttaa  1440
caaataaatc acttaaaagt ttaacttcaa aaaaaaaag gaagaaagaa agaaggtttg  1500
aaattacact atttgcaatt aattatgttt tatgaaaact ttctaatact ttaatttttat  1560 gtcgaatcgt ttgtcgaatc gtttctcttt tatcctacta caaaaatatt ataaaatgat  1620
tataaatggc taaatatat agtatgtgta tttcataaat ttaagaaaat gttttcgaat  1680
acagtcaaat gaactaaaat atttacaaaa atataacaaa atttcatatg tatatcgaat  1740
aaaatttaaa aatttgaaga ctaaatttgt aatataatta catattaaag taattttttag  1800 atgtgtgggt attatataat aataatgttg ggaaggtgag ggcatgaggc agctggaggg  1860
ataaggacta gggattgttt tatatccttt ttcacattta atttttgatg ctaattaatt  1920
tgttgccaat catttcatca ctttttttttt ttttttttggt tctaatttat ttactttata  1980
tggaaaataa ataaaagaaa aatgaaagaa agaaaaaagt ggttttcaaa tcaatagaaa  2040
aaacaaacaa ctccaacttt aatggcttga aaacaaatgc attctaaaat taaaccttat  2100
gattgatttg attttttattc ccctttttta cactttttcat tttcatcata attatatctt  2160
cagttacctg tccaccaatt acaccatcaa atgtggatta ttgggattct ttttttttttt  2220 tttaagatta tcttacggct ttcatttttt tcgtatcttt atgacggttt gatagacgta  2280
aaagtggtta ttgtgttata gagatttgta ttattttgat attatggaag gattcgtttg  2340
agtaaaatta taaaaatcag aggggtgtcg tttaaaaatg taagtaatcc aacacaaaaa  2400
aataattatc ataaaatgta aaaaaaaggg ttagattgaa aacaaacgaa acaaatgagt  2460
tttgtattat aaatcgacct aaaatgttca acccaaacat ggattacgat acgaccgatt  2520
catctcatta cagctcatcg atcctaaaaa tgtgaagaga agtattggat ataattatta  2580
cttaaaaaga taatagaaaa aggaaatcag caaaattagg gttctttaat aagttataaa  2640
actcatttat atacaaaatt aattacatta caaaaggtgg gaatgtggat ttagacatac  2700
```

```
aacctataat aattaattaa aaacaataca catgtttcac aatttgagat aattaaattt    2760
taatccccat ttgataagta atgattttat cttataaatt agtttgttag gtctatactt    2820
tatttgttta tttatttatt cttactcttt tttaattata ttttacttaa tatcccaagc    2880
ttcattaacg attaatctaa gtttgaaatg attaattaca aaatagtagt ctattttgat    2940
ctatcacgga ctattgtggg tattttataa tattttgtta tattttataa atattttag     3000 ttcatttttgc tatatttgaa aataaccata tattatttat attttatttt tctagaaaat   3060 atttttccata aactcaagtt ctatatttaa aatatatatt caaaagtttc ctattacaac   3120
cctaagttga atacttatag aattgtaata aaataagata attaactaaa taagtctaat    3180
taaacactaa taatttgaat taacaacact aaacaaatat tgtcaacaaa acttagttca    3240
attgacatct atatgaagaa tcgagttcca aatcttcaca cctgaacatt aacaaaatta    3300
tatagtaatt atcttaatta attctcctca tcgataaagt gaatatctaa ttaaaaattt    3360
aaagtcaaaa gtgtgaattt cttgaaatat caaattaaga caaaattcaa atcaatttga    3420
aaacatataa acaaaatggt aaattagaca aaaaaaaaaa atcctaaaaa ctacatatga    3480
aaaggttcat taccaaagaa gttttttccat gaaaaaaaaa aagaaagaaa gagaataaaa   3540
tattatatat agttaataat tatgaaattt ttgtataatc ccataaagtt tgcaactaaa    3600
cttaagcata tagtttatga cataattaag gtcactaata atagagaaca gttagagcaa    3660
aggtcaaaca tccactttat tcactctctc tcaatcatac aaagagattt aattgaatct    3720
actcattaca aaatccccaa tcttataata atattaatat cattaatctc ttatatatat    3780 ataataatata tatacatata ttatctcatg cacatggatt ttcatgatct tcaaacccca    3840
cgtcgttgat tttccataaa acctatatat tccactaatc atttatattc attttttttt    3900
ttgggtctaa ttttaaacta tatgttttaa aactccatag tttgatcaat tcaaaaaaaa    3960
aaaaaaaaaa aagtgagtta tacaattttt aaaattttta ggacataatc ttgacaagta    4020
tctttatctc tcctacatga aagagggagc ataagattag cttgacattg tctaaaattg    4080
gaagtgtata tatatatata tatatatcta taaatttaga aattaaaata atggggtttt    4140
ttcatgaaat atatattaat agcttgatta aggaaggttt agagggtgat taaagtgcaa    4200
taatattgtt gattaattgt ttttttttttc ttatgtgtat cttagtttca aggactcatg    4260 ttttttttttt ctttttttctt tttggtccca tggaagagaa cttttttttca attataggat   4320 ttgggttttt agtttttggg aattattgaa aagttataat ttctgttgct aatgatggga    4380
aaattatgaa aaattatata tgcatgggtt ggtggggtca taagatctca aagaagcttt    4440
tattttgtca ttattttttct ttagaaaatc agaatcttaa tctttttttt tttacacatt    4500
ggtattttgg tccctctcg tccaacccaa attaaaaaaa gatcaaaaaa gaaaaaaaaa    4560 aaaaaagaa acagaaacct aatcttaaat caatttccac tatgcaatcc ttaattgtca    4620
tgttgatata aaaaaaaata gtaacgaggc aggagattga accataaaac ttagctttgt    4680
ggttattaat acacttagat gatgctaatt gagttaaact cttgattgac aattaaaaga    4740
aaagttaaat cattagttaa ataattaaag tttaatgatc ataagttaat atttgatgtt    4800
gggtattaat aaaggagatg catttgacta aaaaaatgat taggtagaga ctagggtaat    4860
taataaccaa tattaataaa gtatggttat ggggaattc atgacaaact caagagggga    4920
tgttcatttg ggtcttaatg aagtgtagga attcaaataa tttaaaaagt tattaataat    4980
tattatgatt ttattattat tatttcattt gggtctacat aagtataaag aattgattaa    5040
agaggttgat tatgcagaaa gaagggtgat tagagaagta caattatgaa gggattttgg    5100
```

```
ataaacacat aggaacgaat gattttcatt gggggcctta acaaataata ttcaatttta    5160
aaaaaattga ctatttgcaa ttaggtcttg atcatgaaga tcctcgagat aaattatagt    5220 ttttctttt tttcttcgca tatgaatttg ttcgatataa cgaattttcc gacatatctt    5280
acgtacactg ataagatatt gtctgcttag gatctatact tgtgatttat tctattatct    5340
aatcaatgtg agattttggt ctcattccta acaattctct gctaattaat tgaacaaagg    5400
acgatcactg aggctccatt caaataggaa ctcttatatc taggttaatt actatgctac    5460
attagaacat atcacctatc tgatagagtt caaacacata tcacaccatg agtactactt    5520
tttgaggcta agctccacta catctttgtt tgacacccaa atactctatc tacacgacta    5580
ggttaggagc ataaactttg ataccatctc tttgagacat aaactcccgt cactttattt    5640
ttcatttcat tgatctaaaa cgtcttatac aatagagat agttgttttc acatatatat    5700
acttatatta tcctattgcc tagtgaatct ttatacaaag caacatactt taattttgat    5760
taaacaaaga gtgattacac atggagatca tagcctaatt aaataattaa agtataatta    5820
tagggaggga ttttgagaga aatgtaattc aacaaggatt ttgcataagg gtcttagata    5880
aggaactaaa caactagaaa aaaaaatata atatatatat atataaaagg gaaatgaaat    5940
caaagaaagc atccattctc catatatata aaaatacata tatatatatg gggaagagag    6000
aagagattac aaaactaatt taataataag gtagttgagg gggcaaaaag caaaatacaa    6060
gagattttga tttttgagag aagccctttt tagcaaaaaa aataaaatag attaatataa    6120
cacacaaaca cacacctact cctttttctt c aaccaccaga ttcgatttg cctctctctc    6180 tctctctctc tctctctctc tctgtggatc ttaaacccca attcaaaata tgatgacaaa    6240
ttattaatta ttattcctcc aaaaatattt tccctattaa aaaaaatacc aagagagaga    6300
aaattcaatg attgtttttt ctcttttaca ttattttct tttaaagaaa aaaacttgct    6360
ataaatagag gtgcccattg taagagcaac attcaattca acaaatcttc agttcaattt    6420
ctctcttttt ggctctcaaa aagggaaaga aaaaaaaatc attattatta ttatttcatt    6480
ttctttcttt cccttaaatt tgagctgaag gaaaaaaaaa aaaaaaaaat caatggcgat    6540
tgagattgat attgagcaaa atccaacggt tgaactttcg cgaatcggaa catcagaaac    6600
acacggcgaa gattcgccgt attttgctgg ctggaaagcg tatgatgaag atccttataa    6660
tgaatcaaca aatccttctg gtgttattca aatgggctta gctgaaaatc aagtaagaat    6720
atataacttt ttttgttttt gttttgcttt gtaaggagat tgggtttttt tttttaattg    6780
ggtttgtgtt ggaattatg aaacaggtgt catttgactt attggaggaa tatttggagg    6840
aaaattgtga gggagaaggg aattatttaa attctggggtt tagagaaaat gctttatttc    6900
aagactatca tggtcttttc tcatttagaa gtgcaatggg aagttttatg gaagagatta    6960
gaggtggaag agcaaaattt gacccaaatc gagttgtttt aactgctggt gccactgctg    7020
ccaatgagct tctcactttc attcttgcaa atcctggcga tgctttgctt gtccccactc    7080
cttactatcc tgggtaagtt tatcatcacc tctacgtttt cgtatttcat ttcaaaaacc    7140 actcttact gtaattacta taccctcaga cattaaaatt ttaactttca aactattctt    7200
aaagtatgag tttgagggta tttcatatgg ggttttaaa tgtaaattta tttacattt    7260 tccactactt aagtgtccta tatttctact aatttcttct tgtgttgtac tcatattttc    7320
tatcgtgggg tggactacgt attttacga gactattcgt ataacatacg aatgagtgct    7380
ttttaaacca aattcttcaa aatccaagtt taatttggga aactagaaaa tgggtagttt    7440
tttaaaatgt taccaaacgt gatctttatc cttacaatca aacattacca aggataattg    7500
```

```
caactaccgt tagactttat gagtgctttt ttttccaact gttctatatt tttacaacat    7560
tttgagttgt attcatcatt tctgttaaag atatttatat gtaactaagt attttataa    7620 gacactgttg gtataatttc atgcactaat aatatagttt cttttttccag atttgacaga   7680 gatttgagat ggagaacagg agtgaaaatt gtaccaattc attgtgacag ttcaaacaat   7740
tttcaaataa ctccaaaagc attagaagaa gcttataatt cagcaatgga aatgaaaatc   7800
aaagtaagag gagttttaat cacaaatcca tcaaatccac tcggagcaac gatccaacgc   7860
tccacaatcg aagacattct agatttcgtt acacgcaaaa acatccacct cgtatccgac   7920
gaaatctatt ccggttccgt tttctcctcc gccgagttca caagcgtcgc tgaggttttg   7980
gaatcccgca gctacaaaaa cgccgaacgt gtccacatcg tttacagcct ctccaaagat   8040
ctcggccttc ccgggtttag aatcggcacg atctactcat acaacgataa agtcgtcaca   8100
accgctcgcc ggatgtctag ctttacgctt atctcttcac aaacgcaacg attttagcg    8160 tccatgttgt cgaaccggaa gtttacggag aaatatatta aaatgaaccg gacaggctc    8220 aagaaacggt atgaaatgat tattgaaggg ctgcgaaccg ccgggattga atgtttggaa   8280
gggaatgccg gtttgttttg ttggatgaat ttgagcccgt tgttgaaaga taaaaaaacc   8340
aaagaaggtg agattgagat atggaagagg attttgaagg aagtgaaatt gaatatttcg   8400
cccggttcgt cgtgtcattg ctctgaaccc ggttggttca gggtttgttt tgctaatatg   8460
agtgaaaaga ctctgcatgt tgcccttgat agaatacgtc ggttcatgga acggatgaag   8520
aaggaaaacg aagctaatta aatatatatc tatatataaa tatgtgaaaa gaaaaaaaac   8580
atatgtagct tattttattt tatttttttt tacaatggtt gtgagaaaaa agaaaaaaga   8640
aaaaaaaaag aaaaaaaagc cattgtgatt cttttgtgtg gacactgccc aatatttgtt   8700
agaaatttgg ggtttttttgt cttcatttat acgtcatatt ttgatgattt aaactgagga   8760
aaaagaaaaa gaaatccttg ttttcttgct tttagcaaag caagttttat ttctcagttt   8820
tatatatata tatatataaa gtttctattt gtattgtcat tttatgtgga tatgaaatat   8880
aattagtata attcgttctt gcaattaatt acctcgaaaa taaacgaaat acaagaaaaa   8940
gaaaaaaaaa atctcatgga gtattttagg gacaagtgtc aactcaggga gagagaaaaa   9000
aatatggttt aaatttaata gtattggtta ttttcataac atgctctaaa aaggaatata   9060
actaataatt tgactttaat taagaaaaga aaagctaata atatataatt aaaatcactt   9120
ttagcaacga ataacacttt gccgacttgt gtaattaacc acctaactat ccatctgacg   9180
tggaatgcaa gtaattaatt aattgatttt ttcgttttca aattttggtc aacttgattc   9240
ttggtactaa tttaatgttt ccatctgtca gaaagctaca acgttttttcc tccttctttc   9300 tttttttaaa gaattatttt aaaagtcaa tacggtgcta taattagatt tttattttc    9360 ctcttttta gtgtatatat atatttatat aagtagagat taggaactaa ttgattgaaa    9420
attaaatatg ctgtgacgct caaaagatat taatcccgcg ttggttttat gtatttaaaa   9480
aatgtatttt ttctttttg atattttta ataataaat atttaaatta tttacaaaat     9540
ataacaaaat ttgctcgttt acatttttat tttgtgaagg acttatgcga tgtggttcga   9600
tctagaattc ttgtattttc aaaatagatg gagcttcttt ttggatgaat tctctctagg   9660
cttctgaagt caaaaatttt caacccaaga aaaactaga gtttccttgt ggtatgaggt    9720
gtatgaaatt gactcattga ctcaattaca tggactttta tcatatttaa ctcagctaaa   9780
ttaagtttat tttttggaat taatctaagt aaataatatt taattgaacc aaaatatttta  9840 atttgatcag tcataataaa gacatgtgac atcattggaa tcagtcaatt tgtgtttaaa   9900
```

```
tttaatttgg gatacatgtc aacttttagt taatctcaaa tgcaatttgt gattagttac    9960
aaaatttctt attcaacata cttcaaatct aaatttggta aattatgttt tttttaaaga   10020
aattagatca acacaaaaat ataatatgtt ttgtgaaaat gaaaattttg gtttaatggg   10080
aggagacaaa tttgaacgac aaattttctt agtaacttac gatatgatca ctaactaatt   10140
tattataggt tgggggtttg aacctctctc aactttgtgc tcattatata atatatcttt   10200
aaaagaccga ccttgcatta atgttgttgg ttagtctagt ggtagaatcg tcattctcta   10260
gctctctcta aattgttcca gcttcagttt ttatatactt ttttatatta tttttactga   10320
actataaaaa attactgtcg acaaaattta tgcttttatc acttaacata ataattgaac   10380
tatgtttgct ttgttttttc ttttttaacg tatactatct caaagttttg gataatgtac   10440
gtgtttgaaa tttgtaaaca aacaaggata cataaatacg taattgttgt taattatttc   10500
aaaatgtaaa tagatgatat gatgtagggg ttgctaatat tattgtctaa ttattttttgt   10560
aaagaataaa ataaaataaa aatccatatg atgcctaagg acgtgtttag tattcaatat   10620
ggcgattatt atgtcttttt ttcaaatgga ttacttttttg gatgatatga tatctttat   10680
tttaattaaa acttttttgat gacttttaaa atttaaaggg cataaaatat agctttcttt   10740
tgtacatata tatggttgtg cttggatttt gtatctgctt gtctttgtcc cgagtttctc   10800
gtcggtttga ccttcgatct acttttttttg atatatatgt tccaatatcg atttctaagc   10860
taacatatgt aaaagatgat tgcactcgtg tggtgctgag actatcacac ttgatacttg   10920
ataaagatt gtattattca tctgaaccaa taaaaattaa gatggatatt actcactctt   10980
ctcttttagg atcatcaaac aaggctcttt ttttgacaat cacctgaagt cacgagtaac   11040
tctacagtgt tatagttgtt tatagtattt gagactggaa atatcaaatt cagccaattc   11100
aattaaattt tataattgat atacattcat atgctcgaaa agttggcttc caaccgtcca   11160
acgctctaac tttgggacat gtgttacaaa acacataggt ttaaaaaaat acctaaaaac   11220
ataaaaaata caactttgat catcctttag ttcaatttta ttcccaattt gatacttttg   11280
aattccctaa ctagagaatt gtaattgtga ttgaacgttt ttatagtcaa aatttggatt   11340
tgatagctta taggaccccca tgtgccaaac aaaataaaaa ttgcatatat atatatagag   11400
agagaggggg agttttatat tttaaaaaac aaaattagaa aaaggcaatt aattttgttc   11460
tttaaacgac atggtttctc acgtgttaaa cgtcattgtt atcaactgcg tcttgtcgct   11520
gaccaattca ttgacagcac agcaagcaaa aagaaaaaa gaaaaaaaaa agtcaaaaag   11580
ttaatgtggt taaagaaagc gctttttgtg ataactcaaa aaaacaaacc aaccaatgga   11640
agccctccag gtcactctca tgtggctccc gtctccacgt catcaatgaa cacggacgtg   11700
tttacagctc aacaaacaac aactattcct ctgacgtggc aatttcttat taatgaattt   11760
ccaactctgc cctcctatta cattttctta aggtcggtga atgccgtaca atggaagctc   11820
ctagacatac tttctagttg tgatatatat atatatatat tattcatcca tcatatatta   11880
aactccaatg tatgtttgtg gattttacaa aagttaatat tatttggtag atgttgagat   11940
ttctttttttt tccaatgtct agtctttttc caagttggaa gaaagttttt tatgatgttg   12000
ggagttattt aatttcctag tggggccacg tagttaaata aatataggtt aaattttacg   12060
aaatatccat atatcgcgtg tgtggtatga tttcagttac gtcactattt tgaaaacata   12120
gttttcgtgt tcttattaat gcttatagtt gtaaataaca taattaaaag tatcatttgt   12180
taaaattgat gtcacaccgt atgtacataa tttatttatt gattgatgtt ataaggggcg   12240
ttggagatat cgttggaaaa aaatgatttg taaggatgat cttaattttc tataattgac   12300
```

```
tcacgtatat tatattgtat acgttttca aaatttacac accaatcatc tcactttcgt    12360
tttcattttt cattttagtg gaaaacaatt caataaaaaa aaattctgac aacttttaa    12420
aatttaaggc acagttgaat caatccaacc gttcaagatt taaagaagaa aaaaactaat   12480
ttggttgctc cacttttgt ttttgttcgt tttggtccat taattctaaa aatgtttaat   12540
ttatttgtta tactttcaaa tcttcacaac tttaccgtat tgatccctta aaaatgaagt   12600
aaaaacaata atgaacgaac taagacaatc accatttgaa agtttaagga ccaaatgaac   12660
caaagttaaa agtatagaaa caaaaataaa catcgctaaa taaaccaaat aaaactagaa   12720
ttacttaatt gaaacaaaat aatatgaaat ggatcaaatc tttagactt agtgtatggg    12780
aaagttctat gaaaatgacc accgactatc gagagaccaa ttttggggcc aagtcaatga   12840
ttggtaattt caacctacat ttatgatgta tgacaatgac aatagcttag gtcactttga   12900
aaatgactat aagattttct agttagagat atacacttga tattagactt ggtcgttgta   12960
ataaaaacta tgtgtcacgg atgatatatg ctaagtacat gttttagtct ttaatgtttg   13020
cgtatatttc tttacgtaat ttaatcttcg ttaattatat tttttaaact atgttttaat   13080
cttttaattc ttttgttgtg aaattgacaa ataaagagaa acacgacaat gtagatggta   13140
aacaatgaag tttgtgtagt ttattgacaa tatgttggca atgtttacga gtagagagat   13200
aattgttcaa attacagaac aataggtgac aatacgtgag ttttttgtttt aatttacttt   13260
tgaaacttta ttttgatttt caaaacttaa agaagttgat actattattg ttttgagcta   13320
tgaagatgtg tgatcgaacc tttcacacgt ttagaatgaa agagcatgtc aattaatttt   13380
gagctaaact tgtttaaaaa aattgacctt ttgtctttgt tttaagtttt aacaaattaa   13440
tgatgtcatt gcgtaatttt aagtcagtta ggtatgaaaa gccaccatcg aagaaagaaa   13500
atttcaagaa gaaaagcaat gtagtaaatc acaaataatt gttttctttt cccataggtt   13560
ataactataa aaaaaaaact tcttttttag tataataacg gtaaagaagg atgatcaaac   13620
cttctaactc agtcaattgc aaatatgata aattcacttt gacaaactaa aataaatttg   13680
aagatttatg aaacaaaatg tacattttaa aagtttatat tttcacacaa tgttagcttc   13740
ctttttaaaaa aaaattaaat tttaaaagtt cagagaacaa aacatacatt tcaactttgc   13800
taacttcaat atagaactta tataaaatcg tgccacatag ggttcaaaag aactatagga   13860
ttttaaaatg aaaacatata tttttaattga gttttagaac taagttaata tatttattta   13920
taaagaataa cacttcagta aaattaagaa caacacagac atagttcaat aacataaaac   13980
tagctagagg atccccgggt accatggata tctagaattc gcggccgcaa gcttgatccc   14040
ccgggctgca ggaattcgat atcaagctag agatctagta acatagatga caccgcgcgc   14100
gataattttat cctagtttgc gcgctatatt ttgttttcta tcgcgtatta aatgtataat   14160
tgcgggactc taatcataaa aacccatctc ataaataacg tcatgcatta catgttaatt   14220
attacatgct taacgtaatt caacagaaat tagatgataa tcatcgcaag accggcaaca   14280
ggattcaatc ttaagaaact ttattgccaa atgtttgaac gatctgcagg tcgatcctag   14340
acgcgtgaga tcagatctcg gtgacgggca ggaccgacg gggcggtacc ggcaggctga    14400
agtccagctg ccagaaaccc acgtcatgcc agttcccgtg cttgaagccg ccgcccgca    14460
gcatgccgcg gggggcatat ccgagcgcct cgtgcatgcg cacgctcggg tcgttgggca   14520
gcccgatgac agcgaccacg ctcttgaagc cctgtgcctc cagggacttc agcaggtggg   14580
tgtagagcgt ggagcccagt cccgtccgct ggtggcgggg ggagacgtac acggtcgact   14640
cggccgtcca gtcgtaggcg ttgcgtgcct tccagggcc cgcgtaggcg atgccggcga   14700
```

```
cctcgccgtc cacctcggcg acgagccagg gatagcgctc ccgcagacgg acgaggtcgt   14760
ccgtccactc ctgcggttcc tgcggctcgg tacggaagtt gaccgtgctt gtctcgatgt   14820
agtggttgac gatggtgcag accgccggca tgtccgcctc ggtggcacgg cggatgtcgg   14880
ccgggcgtcg ttctgggctc atggatcgac ctgcaggtct gtcctctcca aatgaaatga   14940
acttccttat atagaggaag ggtcttgcga aggatagtgg gattgtgcgt catcccttac   15000
gtcagtggag atatcacatc aatccacttg ctttgaagac gtggttggaa cgtcttcttt   15060
ttccacgatg ctcctcgtgg gtggggtcc atctttggga ccactgtcgg cagaggcatc   15120
ttcaacgatg gcctttcctt tatcgcaatg atggcatttg taggagccac cttccttttc   15180
cactatcttc acaataaagt gacagatagc tgggcaatgg aatccgagga ggtttccgga   15240
tattacccct tgttgaaaag tctcaattgc cctttggtct tctgagactg tatctttgat   15300 attttggag tagacaagcg tgtcgtgctc caccatgttg acggatctct agcttatcga   15360
taccgtcggc tattggtaat aggacactgg gattcgtctt ggacaacttt ccttctcatc   15420
taagcgtaga caaccctcaa ctggaaacgg gccggactcc agggcgtgtg ccaggtgccc   15480
acggaatagt tttggccaga cccttgaaaa tccgattcag tacaatcgat tgccctcatt   15540
tttacgttgg catatatcct gccaaacagc caacaacgcg cgtgcggtga ataggaaagc   15600
gtttgagttg cttgctcata tcgtgacggt tgacagcaca ggttaccgc ttgatgattc   15660 gtacgagccg ccaaacattg gctgtcgtaa tgatatacca tgtcagaaca gcaatccgat   15720
ggggcggaaa gcattatctt aatgcacacg gaaatggcgc gtcggtgggt ggaatacacc   15780
gacatagagg ccgtaagttc tgcatggtca tcgtcggaaa ggtggcagca ggcgcacggc   15840
tgtggcctct tgctctttca gcgtgaaatg cgtgttgaaa gaataatcga agagagcgtc   15900
cgctcgacac cttcaattat gccgatttga tcgatgaact gatcgagctc tgaaatcgaa   15960
ggggcttcga taatcgcaat caaatcaaaa gtgccactca cagaatgaag agcgataacg   16020
gccgtgacct tcccaaggga ggccgtcacc tgtgaaagcg ccttcgtaat ggtgatcaga   16080
atatgggctc gaaccaagct cgagacctcg agggggggcc cggtacccaa ttcgccctat   16140
agtgagtcgt attacaattc actggccgtc gttttac                            16177
```

<210> SEQ ID NO 8
<211> LENGTH: 445
<212> TYPE: PRT
<213> ORGANISM: Cucumis melo

<400> SEQUENCE: 8

```
Met Ala Ile Glu Ile Asp Ile Glu Gln Asn Pro Thr Val Glu Leu Ser
1               5                   10                  15

Arg Ile Gly Thr Ser Glu Thr His Gly Glu Asp Ser Pro Tyr Phe Ala
            20                  25                  30

Gly Trp Lys Ala Tyr Asp Glu Asp Pro Tyr Asn Glu Ser Thr Asn Pro
        35                  40                  45

Ser Gly Val Ile Gln Met Gly Leu Val Glu Asn Gln Val Ser Phe Asp
    50                  55                  60

Leu Leu Glu Glu Tyr Leu Glu Glu Asn Cys Glu Gly Glu Gly Asn Tyr
65                  70                  75                  80

Leu Asn Ser Gly Phe Arg Glu Asn Ala Leu Phe Gln Asp Tyr His Gly
                85                  90                  95

Leu Phe Ser Phe Arg Ser Ala Met Gly Ser Phe Met Glu Glu Ile Arg
            100                 105                 110

Gly Gly Arg Ala Lys Phe Asp Pro Asn Arg Val Val Leu Thr Ala Gly
```

```
                115                 120                 125
Ala Thr Ala Ala Asn Glu Leu Leu Thr Phe Ile Leu Ala Asn Pro Gly
130                 135                 140

Asp Ala Leu Leu Val Pro Thr Pro Tyr Tyr Pro Gly Phe Asp Arg Asp
145                 150                 155                 160

Leu Arg Trp Arg Thr Gly Val Lys Ile Val Pro Ile His Cys Asp Ser
                165                 170                 175

Ser Asn Asn Phe Gln Ile Thr Pro Lys Ala Leu Glu Glu Ala Tyr Asn
                180                 185                 190

Ser Ala Met Glu Met Lys Ile Lys Val Arg Gly Val Leu Ile Thr Asn
                195                 200                 205

Pro Ser Asn Pro Leu Gly Ala Thr Ile Gln Arg Ser Thr Ile Glu Asp
210                 215                 220

Ile Leu Asp Phe Val Thr Arg Lys Asn Ile His Leu Val Ser Asp Glu
225                 230                 235                 240

Ile Tyr Ser Gly Ser Val Phe Ser Ser Ala Glu Phe Thr Ser Val Ala
                245                 250                 255

Glu Val Leu Glu Ser Arg Ser Tyr Lys Asn Ala Glu Arg Val His Ile
                260                 265                 270

Val Tyr Ser Leu Ser Lys Asp Leu Gly Leu Pro Gly Phe Arg Ile Gly
                275                 280                 285

Thr Ile Tyr Ser Tyr Asn Asp Lys Val Val Thr Ala Arg Arg Met
290                 295                 300

Ser Ser Phe Thr Leu Ile Ser Ser Gln Thr Gln Arg Phe Leu Ala Ser
305                 310                 315                 320

Met Leu Ser Asn Arg Lys Phe Thr Glu Lys Tyr Ile Lys Met Asn Arg
                325                 330                 335

Asp Arg Leu Lys Lys Arg Tyr Glu Met Ile Ile Glu Gly Leu Arg Thr
                340                 345                 350

Ala Gly Ile Glu Cys Leu Glu Gly Asn Ala Gly Leu Phe Cys Trp Met
                355                 360                 365

Asn Leu Ser Pro Leu Leu Lys Asp Lys Lys Thr Lys Glu Gly Glu Ile
370                 375                 380

Glu Ile Trp Lys Arg Ile Leu Lys Glu Val Lys Leu Asn Ile Ser Pro
385                 390                 395                 400

Gly Ser Ser Cys His Cys Ser Glu Pro Gly Trp Phe Arg Val Cys Phe
                405                 410                 415

Ala Asn Met Ser Glu Lys Thr Leu His Val Ala Leu Asp Arg Ile Arg
                420                 425                 430

Arg Phe Met Glu Arg Met Lys Lys Glu Asn Glu Ala Asn
                435                 440                 445

<210> SEQ ID NO 9
<211> LENGTH: 27
<212> TYPE: DNA
<213> ORGANISM: Cucumis melo

<400> SEQUENCE: 9
acattcaatt caacaaatct tcagttc                                    27

<210> SEQ ID NO 10
<211> LENGTH: 27
<212> TYPE: DNA
<213> ORGANISM: Cucumis melo

<400> SEQUENCE: 10
```

```
gggtatagta attacagtaa agagtgg                                          27

<210> SEQ ID NO 11
<211> LENGTH: 70
<212> TYPE: DNA
<213> ORGANISM: Cucumis melo

<400> SEQUENCE: 11
aatcaacaaa tccttctggt gttattcaaa tgggcttagc tgaaaatcaa gtgtcatttg      60
acttattgga                                                            70

<210> SEQ ID NO 12
<211> LENGTH: 70
<212> TYPE: DNA
<213> ORGANISM: Cucumis melo

<400> SEQUENCE: 12
aatcaacaaa tccttctggt gttattcaaa tgggcttagt tgaaaatcaa gtgtcatttg      60
acttattgga                                                            70

<210> SEQ ID NO 13
<211> LENGTH: 40
<212> TYPE: PRT
<213> ORGANISM: Cucumis melo

<400> SEQUENCE: 13

Ala Gly Trp Lys Ala Tyr Asp Glu Asp Pro Tyr Asn Glu Ser Thr Asn
1               5                   10                  15

Pro Ser Gly Val Ile Gln Met Gly Leu Ala Glu Asn Gln Val Ser Phe
            20                  25                  30

Asp Leu Leu Glu Glu Tyr Leu Glu
        35                  40

<210> SEQ ID NO 14
<211> LENGTH: 40
<212> TYPE: PRT
<213> ORGANISM: Cucumis melo

<400> SEQUENCE: 14

Ala Gly Trp Lys Ala Tyr Asp Glu Asp Pro Tyr Asn Glu Ser Thr Asn
1               5                   10                  15

Pro Ser Gly Val Ile Gln Met Gly Leu Val Glu Asn Gln Val Ser Phe
            20                  25                  30

Asp Leu Leu Glu Glu Tyr Leu Glu
        35                  40

<210> SEQ ID NO 15
<211> LENGTH: 40
<212> TYPE: PRT
<213> ORGANISM: Arabidopsis thaliana

<400> SEQUENCE: 15

His Gly Trp Lys Ala Tyr Asp Asn Asn Pro Phe His Pro Thr His Asn
1               5                   10                  15

Pro Gln Gly Val Ile Gln Met Gly Leu Ala Glu Asn Gln Leu Cys Ser
            20                  25                  30

Asp Leu Ile Lys Glu Trp Ile Lys
        35                  40

<210> SEQ ID NO 16
<211> LENGTH: 40
```

```
<212> TYPE: PRT
<213> ORGANISM: Arabidopsis thaliana

<400> SEQUENCE: 16

Asp Gly Trp Lys Ala Tyr Asp Lys Asp Pro Phe His Leu Ser Arg Asn
1               5                   10                  15

Pro His Gly Ile Ile Gln Met Gly Leu Ala Glu Asn Gln Leu Cys Leu
            20                  25                  30

Asp Leu Ile Lys Asp Trp Val Lys
        35                  40

<210> SEQ ID NO 17
<211> LENGTH: 40
<212> TYPE: PRT
<213> ORGANISM: Arabidopsis thaliana

<400> SEQUENCE: 17

Leu Gly Trp Glu Glu Tyr Glu Lys Asn Pro Tyr Asp Val Thr Lys Asn
1               5                   10                  15

Pro Gln Gly Ile Ile Gln Met Gly Leu Ala Glu Asn Gln Leu Cys Phe
            20                  25                  30

Asp Leu Leu Glu Ser Trp Leu Ala
        35                  40

<210> SEQ ID NO 18
<211> LENGTH: 40
<212> TYPE: PRT
<213> ORGANISM: Arabidopsis thaliana

<400> SEQUENCE: 18

Leu Gly Trp Glu Glu Tyr Glu Lys Asn Pro Tyr Asp Glu Ile Lys Asn
1               5                   10                  15

Pro Asn Gly Met Ile Gln Met Gly Leu Ala Glu Asn Gln Leu Cys Phe
            20                  25                  30

Asp Leu Ile Glu Ser Trp Leu Thr
        35                  40

<210> SEQ ID NO 19
<211> LENGTH: 40
<212> TYPE: PRT
<213> ORGANISM: Arabidopsis thaliana

<400> SEQUENCE: 19

Asp Gly Trp Lys Ala Tyr Glu Glu Asn Pro Phe His Pro Ile Asp Arg
1               5                   10                  15

Pro Asp Gly Val Ile Gln Met Gly Leu Ala Glu Asn Gln Leu Cys Gly
            20                  25                  30

Asp Leu Met Ala Lys Trp Val Leu
        35                  40

<210> SEQ ID NO 20
<211> LENGTH: 40
<212> TYPE: PRT
<213> ORGANISM: Arabidopsis thaliana

<400> SEQUENCE: 20

Ala Gly Trp Lys Ala Tyr Asp Glu Asn Pro Tyr Asp Glu Ser His Asn
1               5                   10                  15

Pro Ser Gly Val Ile Gln Met Gly Leu Ala Glu Asn Gln Val Ser Phe
            20                  25                  30

Asp Leu Leu Glu Thr Tyr Leu Glu
```

```
                35                  40

<210> SEQ ID NO 21
<211> LENGTH: 40
<212> TYPE: PRT
<213> ORGANISM: Arabidopsis thaliana

<400> SEQUENCE: 21

Trp Gly Trp Glu Glu Tyr Glu Lys Asn Pro Tyr Asp Glu Ile Lys Asn
1               5                   10                  15

Pro Asp Gly Ile Ile Gln Met Gly Leu Ala Glu Asn Gln Leu Ser Phe
            20                  25                  30

Asp Leu Ile Glu Ser Trp Leu Ala
        35                  40

<210> SEQ ID NO 22
<211> LENGTH: 40
<212> TYPE: PRT
<213> ORGANISM: Arabidopsis thaliana

<400> SEQUENCE: 22

Leu Gly Trp Glu Glu Tyr Glu Lys Asn Pro Tyr Asp Glu Ile Lys Asn
1               5                   10                  15

Pro Asn Gly Ile Ile Gln Met Gly Leu Ala Glu Asn Gln Leu Cys Phe
            20                  25                  30

Asp Leu Ile Glu Thr Trp Leu Ala
        35                  40

<210> SEQ ID NO 23
<211> LENGTH: 38
<212> TYPE: PRT
<213> ORGANISM: Arabidopsis thaliana

<400> SEQUENCE: 23

Val Gly Gln Lys Arg Val Glu Asp Pro Tyr Asp Glu Leu Gly Asn
1               5                   10                  15

Pro Asp Gly Val Ile Gln Leu Gly Leu Ala Gln Asn Asn Lys Leu Ser
            20                  25                  30

Leu Asp Asp Trp Val Leu
        35

<210> SEQ ID NO 24
<211> LENGTH: 40
<212> TYPE: PRT
<213> ORGANISM: Arabidopsis thaliana

<400> SEQUENCE: 24

Leu Gly Trp Gln Glu Tyr Glu Lys Asn Pro Phe His Glu Ser Phe Asn
1               5                   10                  15

Thr Ser Gly Ile Val Gln Met Gly Leu Ala Glu Asn Gln Leu Ser Phe
            20                  25                  30

Asp Leu Ile Glu Lys Trp Leu Glu
        35                  40

<210> SEQ ID NO 25
<211> LENGTH: 40
<212> TYPE: PRT
<213> ORGANISM: Arabidopsis thaliana

<400> SEQUENCE: 25

Ile Gly Leu Glu Arg Val Lys Thr Asp Pro Tyr Asp Arg Ile Thr Asn
1               5                   10                  15
```

```
Thr Asp Gly Ile Ile Gln Leu Gly Leu Ala Glu Ser Thr Leu Cys Phe
            20                  25                  30

Asp Leu Leu Gln Arg Trp Met Ser
            35              40
```

GENETIC SYSTEM FOR CONTROLLING THE FLORAL DEVELOPMENT OF A DICOTYLEDON PLANT, AND IMPLEMENTATION IN DETECTION AND SELECTION PROCESSES

FIELD OF THE INVENTION

The present invention relates to the selection of plant varieties, and in particular to the selection of the sex type of plants. It relates to genotypic plant sex detection by analysing the polymorphism of a gene A, as well as to means for implementing such detection and to methods for producing plants which sex phenotype has been modified.

PRIOR ART

The production of hybrid plants represents a very worthwhile activity in the world of agronomy and agriculture. Indeed, hybrid plants, thanks to a phenomenon called heterosis, also known as hybrid vigor, do exceed their parents in many characters as compared to the average of both of them. Such superiority may be illustrated for example by a stronger vigor, a better yield, a higher adaptation to the environment where the hybrid is cultured, and a high uniformity amongst the hybrids as compared to their parents. Such hybrid vigor is all the more marked that the parents are genetically distant.

Producing pure and stable plant variety lines, that will be the future parents for the hybrid is a necessary condition for generating homogenous and reproducible hybrid varieties expressing maximum heterosis. It is therefore required to produce pure and stable plant variety lines, then to cross-breed these lines to obtain hybrids.

The production of pure plant variety lines involves the self-fertilization of a plant in order to obtain plants having a common genetic hereditary material, fixed for the whole expected characters of productivity, yield regularity or resistance to disease.

To produce pure plant variety lines, it is therefore necessary to use plants which sex type enables self-fertilization, for example hermaphroditic plants.

However, many dicotyledon plants, and in particular cucurbitaceae may be monoecious, andromonoecious, gynoecious or hermaphroditic.

A first implementation means, for producing pure plant lines, does consist in conducting a chemical treatment on the plants, so that plants that have the ability to self-fertilize are obtained, for example hermaphroditic plants. For melon (*cucumis melo*) for example, spraying inhibitors of ethylene synthesis such as silver nitrate or silver thiosulfate causes stamina to temporarily appear in female flowers (Rudich and al., 1969; Risser and al., 1979). In this way, converting gynoic plants to bisexual plants makes it possible to maintain pure lines.

However, the production of pure lines using such method is limited by the high cost of the chemical agents, as well as by their persistency and their phytotoxic effects. Moreover, such agents may be ineffective as regards the production of hybrids starting from plants which flowering time is long-lasting, because new flowers that would appear after the treatment could be not affected by the chemical treatment.

There is therefore a need for a system which would enable to control the floral development of a dicotyledon plant, and to obtain a plant of a determined floral type.

In addition, very many cross-breedings are required to obtain interesting hybrids, starting from pure lines, and in each cross-breeding, the plants with the most promising phenotype are retained.

When inter-breeding pure lines, it is essential to be able to choose the way the cross-breeding is effected, so as to prevent plant self-pollination which would lead to plants deprived of the expected hybrid vigor.

Once again, because of the dicotyledon plant sex type diversity, it is necessary to separate male and female flowers from the same seedling so as to avoid self-pollination.

A first method, in particular implemented for corn, does consist in using mechanical means for carrying out a plant emasculation. However, such method reveals extremely expensive as it does require to emasculate each plant for which self-pollination is to be avoided, for each cross-breeding done.

Another method does consist in performing a chemical emasculation of the plants, blocking the formation of viable pollen. Thus, in melon (*Cucumis melo*), treating monoecious plants with ethrel (ethylene precursor) causes the male flowers to temporarily disappear.

Such chemical agents, called gametocydal agents, used to cause a transitional male sterility suffer from several drawbacks, like a high cost or a high toxicity, as previously already mentioned.

The hereabove described mechanical or chemical methods for controlling the floral type thus reveal to be very expensive, all the more so as very numerous cross-breedings are required to obtain hybrid plants having the expected characters and suitable for being marketed.

To help producing pure and hybrid lines, there is therefore also a need for a system which would enable to control the floral development of a dicotyledon plant, and to obtain a plant of a determined floral type.

Another method to obtain plants that are able to self-pollinate and useful for producing pure lines, or that are not able to self-pollinate, for producing hybrids, could respectively consist in selecting exclusively bisexual individuals or exclusively female individuals present within one species. However, such a method would also reveal very expensive, since it would require to culture a great number of plants, until it would become possible to determine the sex type thereof. Moreover, such a method would be uncertain, because the mechanisms for determining the sex of flowers do in particular depend on environmental factors.

There is therefore also a need for providing a method which would enable to select dicotyledon plants for example bisexual or female, without necessarily requiring their culture.

This method should enable to select plants especially useful for producing pure or hybrid lines as previously stated hereabove.

SUMMARY OF THE INVENTION

The present invention provides a system which enables the floral development of a dicotyledon plant to be controlled. The present inventors showed that two genetic control elements, (A/a) and (G/g) both possessing at least two alleles, (A) and (a) for the first genetic element and (G) and (g) for the second genetic element, contribute to control the sex determinism in cucurbitaceae.

The present inventors also showed that, at the physiological level, both alleles (A) and (a), do differ from each other through different concentrations of a new protein.

It is therefore an object of the present invention to provide a genetic system for controlling the type of floral development of a dicotyledon plant, the said system including the combination of two genetic control elements, respectively:

a first genetic control element (A/a) present in a dicotyledon plant, in the form of a dominant allele (A), and a recessive allele (a), wherein:
the dominant allele (A) consists of a nucleic acid (NA) comprising:
(i) a regulatory polynucleotide (PA) that is functional in a dicotyledon plant, and
(ii) a nucleic acid which expression is regulated by the regulatory polynucleotide (PA), the said nucleic acid encoding the ACCS protein of SEQ ID No 3,
the recessive allele (a) differs from the dominant allele (A) through:
(i) a nucleic acid (NA) that is not present in the plant, or
(ii) a regulatory polynucleotide (Pa) that is not functional in a dicotyledon plant, or
(iii) a nucleic acid encoding a non active ACCS protein, or
(iv) a regulatory polynucleotide (Pa) that is not functional in a dicotyledon plant, and a nucleic acid encoding a non active ACCS protein, and a second genetic control element (G/g) present in a dicotyledon plant, in the form of a dominant allele (G), and a recessive allele (g), wherein:
the dominant allele (G) consists of a nucleic acid (NG) which expression results in the development of an andromonoecious or a monoecious plant, and
the recessive allele (g) differs from the dominant allele (G) through:
(i) a nucleic acid (NG) that is not present in the plant, or
(ii) the presence of a nucleic acid (Ng) which expression, in a dicotyledon plant, results in the development of a hermaphroditic or a gynoecious plant, provided that the first genetic control element has been artificially inserted into the said dicotyledon plant.

It is a further object of the present invention to provide the regulatory polynucleotides (PA) and (Pa) as such.

The present invention also relates to methods for producing a transformed plant which sex phenotype has been modified, as well as the various parts of such plant, especially seeds thereof.

It is yet a further object of the present invention to provide ACCS protein such as defined in more details hereunder, or a fragment of said protein, as well as antibodies directed against ACCS protein.

The present invention also relates to methods for detecting the presence of the alleles (A) and (a) in a sample.

BRIEF DESCRIPTION OF THE DRAWINGS

FIG. 1A is a nucleotide sequence analysis of the (A) and (a) alleles in a portion of the ACCS gene of *Cucumis melo*, showing a C/T single nucleotide polymorphism.

FIG. 1B is an amino acid sequence analysis of the (A) and (a) alleles of the ACCS protein of *Cucumis melo*, showing an Ala57Val substitution, and homologous proteins from *Arabidopsis thaliana*.

DETAILED DESCRIPTION OF THE INVENTION

Figure 2:
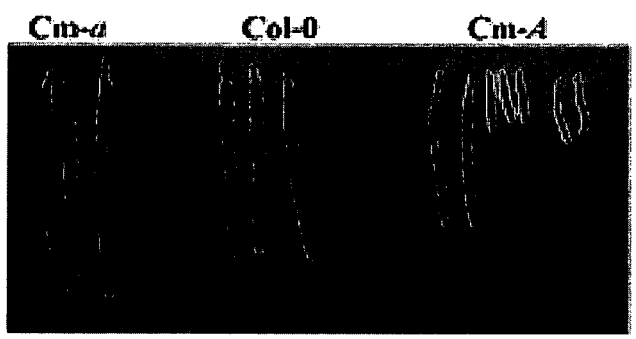
FIG. 2A is a photograph comparing siliqua from *Arabidopsis thaliana* transformed with alleles (a) or (A) of the ACCS gene of *Cucumis melo*, compared to control (Col-0).
FIG. 2B is a photograph showing the effects on the flower of *Arabidopsis thaliana* transformed with allele (a) of the ACCS gene of *Cucumis melo*.
Figure 2:

The present inventors have shown that two genetic control elements, (A/a) and (G/g), both possessing at least two alleles, (A) and (a) for the first genetic element and (G) and (g) for the second genetic element, contribute to control the sex determinism in cucurbitaceae.

It has been demonstrated by the present inventors that the allele (A) controls the andromonoecious character of plants, and that the allele (G) controls the gynoecious character of plants, as illustrated in Table 1 hereunder.

TABLE 1

| Phenotype | Genotype | Flower type |
|---|---|---|
| Monoecious | AAGG or Aa GG | Male and female |
| Andromonoecious | aaGG | Male and hermaphrodite |
| Hermaphroditic | aagg | hermaphrodite |
| Gynoecious | AAgg or Aagg | Female |

Table 1 illustrates the relation that exists between the genotype and the sex phenotype of flowers of dicotyledon plants.

The present inventors have also shown that on the physiological level, both alleles (A) and (a), do differ from each other through different concentrations of a new protein.

In particular, the present inventors have shown that on the physiological level, in *Cucumis melo*, both alleles (A) and (a), do differ through different concentrations of a new protein, of the ACCS type, involved in ethylene metabolism.

Yet, various studies showed that genes in floral biology of cucurbitaceae do encode proteins involved in the biosynthesis or ethylene regulation pathway (Kamachi and al., 1997; Kahana and al., 2000).

The present inventors have shown that the allele (a) does differ on the physiological level from the allele (A) through a low ACCS protein level in the plant, as compared to that of a plant having an allele (A).

From a genetic point of view, the present inventors have shown that the allele (A) does differ from the allele (a) through a difference in the promoter sequence of the sequence encoding ACCS protein. To the mind of the inventors, this difference, precisely, does induce a distinct protein level for both alleles (A) and (a) as well as a distinct sex phenotype.

The present inventors also have shown in Example 1 that the allele (A) does also differ from the allele (a) through a difference in the ACCS protein sequence itself. Indeed the allele (A) is associated with the presence of an alanine residue at position 57 of the sequence encoding ACCS protein, and the allele (a) is associated with the presence of a valine residue at position 57 of that same sequence.

The present inventors have also shown in Example 2 that this difference in the promoter region, and in the protein sequence itself does result in a distinct temporal and spatial expression of the ACCS protein, for both alleles.

Without wishing to be bound by any particular theory, the present inventors believe that the control system according to the present invention may be generalized to any dicotyledon plant, for which sex determination depends on the ethylene concentration as already stated hereabove.

Indeed, the present inventors have shown in Example 3 that expressing the allele (A) or the allele (a) in a dicotyledon plant that does not belong to the cucurbitaceae family makes it possible to respectively obtain a gynoecious or an hermaphroditic phenotype.

Finally, the present inventors have determined that the allele (A) is dominant over the allele (a).

It is therefore an object of the present invention to provide a genetic system for controlling the type of floral development of a dicotyledon plant, the said system comprising the combination of two genetic control elements, respectively:

- a first genetic control element (A/a) present in a dicotyledon plant, in the form of a dominant allele (A), and a recessive allele (a), wherein:
  - the dominant allele (A) consists of a nucleic acid (NA) comprising:
    - (i) a regulatory polynucleotide (PA) that is functional in a dicotyledon plant, and
    - (ii) a nucleic acid which expression is regulated by the regulatory polynucleotide (PA), the said nucleic acid encoding the ACCS protein of SEQ ID No 3,
  - the recessive allele (a) differs from the dominant allele (A) through:
    - (i) a nucleic acid (NA) that is not present in the plant, or
    - (ii) a regulatory polynucleotide (Pa) that is not functional in a dicotyledon plant, or
    - (iii) a nucleic acid encoding a non active ACCS protein, or
    - (iv) a regulatory polynucleotide (Pa) that is not functional in a dicotyledon plant, and a nucleic acid encoding a non active ACCS protein, and
- a second genetic control element (G/g) present in a dicotyledon plant, in the form of a dominant allele (G), and a recessive allele (g), wherein:
  - the dominant allele (G) consists of a nucleic acid (NG) which expression results in the development of an andromonoecious or a monoecious plant, and
  - the recessive allele (g) differs from the dominant allele (G) through:
    - (i) a nucleic acid (NG) that is not present in the plant, or
    - (ii) the presence of a nucleic acid (Ng) which expression, in a dicotyledon plant, results in the development of a hermaphroditic or a gynoecious plant, provided that the first genetic control element has been artificially inserted into the said dicotyledon plant.

The genetic control system identified by the inventors enables the sex of the flowers of dicotyledon plants to be controlled and/or modified, and is thus very advantageous, as compared to mechanical control systems, that are often expensive, or to chemical control systems, that are often toxic, such as described in the introduction section.

As used herein, an "allele" is intended to mean one of the forms of a gene located in a site or locus on a pair of homologous chromosomes. The alleles of a gene do relate to the same genetic trait but they may determine different phenotypes.

A dominant allele is an allele, the phenotype expression level of which is much higher than that of the homologous allele (the so called recessive allele). The dominance may be complete or partial.

A recessive allele is an allele, which corresponding phenotype expresses only when the plant receives the same alleles from each of both parents thereof. By contrast, the expression of the recessive allele is masked if the homologous dominant allele is present.

Thus, the hereabove defined system does exist in the form of various states, each corresponding to one phenotype.

When the first genetic control element (A/a) present in a dicotyledon plant is in the form of the allele (A), the plant has a monoecious or a gynoecious phenotype.

When the first genetic control element (A/a) present in a plant is in the form of the allele (a), the plant has a hermaphroditic or an andromonoecious phenotype.

When the second genetic control element (G/g) present in a dicotyledon plant is in the form of the allele (G), the plant has a monoecious or an andromonoecious phenotype.

When the second genetic control element (G/g) present in a plant is in the form of the allele (g), the plant has a hermaphroditic or a gynoecious phenotype.

The relation that exists between alleles and phenotypes is summarized in Table 1.

The description that follows illustrates alternatives or preferred embodiments of the first and second genetic control elements that belong to the control system according to the invention.

Genetic Control Element A/a, in the Form of the Dominant Allele (A) of the System of the Invention Generally speaking, the genetic control element A/a, present in a plant in the form of the dominant allele (A), makes it possible to obtain a higher amount level of ACCS protein, as compared to the amount level observed when the allele (A) is not present in said plant.

In the following description, a "high level of ACCS protein" does correspond to the average amount level of ACCS protein measured in a plant comprising the dominant allele (A) within its genome, and a "low level of ACCS protein" does correspond to the average amount level of ACCS protein observed in a plant not comprising the dominant allele (A) within its genome.

The dominant allele (A) consists of a nucleic acid (NA) comprising:
(i) a regulatory polynucleotide (PA) that is functional in a dicotyledon plant, and
(ii) a nucleic acid which expression is regulated by the regulatory polynucleotide (PA), the said nucleic acid encoding the ACCS protein of SEQ ID No 3.

Functional Regulatory Polynucleotide (PA)

A functional regulatory polynucleotide (PA) or promoter according to the present invention consists of a nucleic acid which enables the ACCS protein of SEQ ID No 3 to be expressed in dicotyledon plants.

As an example, such a promoter comprises a nucleotide sequence extending from nucleotide 1 to nucleotide 5906 of the SEQ ID No 1.

Thus, it is an object of the present invention to provide a genetic control system wherein the regulatory polynucleotide (PA) comprises or consists in a nucleotide sequence extending from nucleotide 1 to nucleotide 5906 of the SEQ ID No 1.

It is a further object of the present invention to provide the hereabove defined regulatory polynucleotide (PA) as such, as well as fragments of such nucleic acid, as it will be described in more details in the section entitled "Nucleic acids of the invention".

A functional regulatory polynucleotide (PA) according to the present invention may also consist of a promoter known for directing the expression of the nucleic acid sequence encoding the ACCS protein in a constitutive manner (constitutively) or in a tissue-specific manner.

A functional regulatory polynucleotide (PA) according to the present invention may thus be selected from tissue-specific promoters such as those from the "MADS box" gene family (class A B C D and E), such as described by Theißen and al., 2001, or any other homeotic gene promoter.

A functional regulatory polynucleotide (PA) according to the present invention may thus be selected from:

The cauliflower mosaic virus 35S promoter, or the 19S promoter or advantageously the double 35S constitutive promoter (pd35S), described in the article written by Kay and al., 1987;

The rice actin promoter followed with the rice actin intron (pAR-IAR) contained in plasmid pAct1-F4 described by Mc Elroy and al., 1991;

The constitutive promoter EF-1α of the gene encoding the plant elongation factor described in the PCT application WO 90/02172 or in the article written by AXELOS and al. (1989);

The chimeric super-promoter PSP (NI and al., 1995) based on the three copy-fusion of a transcription activation element of the *Agrobacterium tumefaciens* octopine synthase gene promoter and of a transcription activation element of the *Agrobacterium tumefaciens* mannopine synthase gene promoter, and the sunflower ubiquitin promoter (BINET and al., 1991);
the maize ubiquitin 1 promoter (CHRISTENSEN and al., 1996).

A functional regulatory polynucleotide (PA) according to the present invention may also consist of an inducible promoter.

Thus, it is an object of the present invention to provide a control system such as defined hereabove, wherein the regulatory polynucleotide (PA) is sensitive to the action of an induction signal, and preferably, wherein the regulatory polynucleotide (PA) is an inducible, transcription or translation-activating polynucleotide.

When the transcription or translation-activating regulatory polynucleotide is sensitive, either directly or indirectly, to the action of an activating induction signal, it is an "inducible activating or activator" polynucleotide as defined in the present invention.

According to the invention, a regulatory polynucleotide of the "inducible activating" type is a regulatory sequence which is only activated in the presence of an external signal. Such an external signal may be the binding of a transcription factor, where the binding of a transcription factor may be induced by the activating induction signal to which the regulatory polynucleotide is directly or indirectly sensitive.

When such a nucleic acid construct is used in a host cell, the expression of the polynucleotide encoding the ACCS protein according to the present invention may be induced by bringing the transformed host cell into contact with the activating induction signal to which the activating regulatory polynucleotide is, directly or indirectly, sensitive.

When the absence of expression of the polynucleotide encoding an ACCS protein is expected in this transformed host cell, the presence of the activating induction signal to which the transcription or translation-activating regulatory polynucleotide is sensitive simply has to be eliminated or removed.

It is within the technical general knowledge of the man skilled in the field of regulatory polynucleotides, and especially those regulatory polynucleotides which are active in plants, to define the constructs corresponding to the definition of the hereabove embodiment.

The regulatory sequence capable of controlling the nucleic acid encoding an ACCS protein may be a regulatory sequence inducible by a particular metabolite, such as:

a glucocorticoid-inducible regulatory sequence such as described by AOYAMA and al. (1997) or such as described by McNELLYS and al. (1998);

an ethanol-inducible regulatory sequence, such as the one described by SALTER and al. (1998) or such as described by CADDICK and al. (1998);

a tetracycline-inducible regulatory sequence such as the one marketed by the CLONTECH company;

a promoter sequence inducible by a pathogenic agent or by a metabolite produced by a pathogenic agent;

a salicylic acid- or BTH- or aliette-inducible regulatory sequence of PR type genes (Gorlach and al., 1996, Molina and al., 1998);

a tebufenozide-inducible regulatory sequence of the ecdysone receptor type (Martinez and al., 1999) (product reference RH5992, marketed by the ROHM & HAAS company) for example, belonging to the dibenzoylhydrazine family.

Nucleic Acids Encoding the ACCS Protein

Preferably, the nucleic acid encoding the ACCS protein comprises, from the 5' end to the 3' end, at least:

(i) one sequence having at least 95% identity with the polynucleotide extending from nucleotide 5907 to nucleotide 6086 of the SEQ ID No 1, (ii) one sequence having at least 95% identity with the polynucleotide extending from nucleotide 6181 to nucleotide 6467 of the SEQ ID No 1, and (iii) one sequence having at least 95% identity with the polynucleotide extending from nucleotide 7046 to nucleotide 7915 of the SEQ ID No 1.

Genetic Control Element A/a, in the Form of a Recessive Allele (a) of the System of the Invention Generally speaking, the genetic control element (A/a) in the form of the recessive allele (a), when present in a plant not possessing the dominant allele (A) within its genome, does not enable to obtain an ACCS protein level as high as the one which is obtained when the allele (A) is present.

Therefore the allele (a) may be defined as any alteration of the genotype corresponding to the allele (A), which does not enable to obtain an ACCS protein level as high as the allele (A).

The recessive allele (a) differs from the dominant allele (A) through:

(i) a nucleic acid (NA) that is not present in the plant, or
(ii) a regulatory polynucleotide (Pa) that is not functional in a dicotyledon plant, or
(iii) a nucleic acid encoding a non active ACCS protein, or
(iV) a regulatory polynucleotide (Pa) that is not functional in a dicotyledon plant, and a nucleic acid encoding a non active ACCS protein.

Non Functional Regulatory Polynucleotide (Pa)

A non functional regulatory polynucleotide (Pa) or promoter according to the present invention is a nucleic acid which:

(i) does not allow the expression of the ACCS protein of SEQ ID No 3 in a host cell, or
(ii) allows this protein to be expressed at a low level as compared to the level observed with the regulatory polynucleotide (PA), or
(iii) allows the ACCS protein to be expressed during the plant life, for a shorter time period as compared to the expression time period observed with the regulatory polynucleotide (PA).

There is a simple method to compare the expression level of several promoters, which is known from the man skilled in the art and which consists in placing a selectable marker gene under the control of the promoters to be tested. A selectable marker gene may be for example the BASTA herbicide resistance gene, well known from the one skilled in the art.

Another method may consist of measuring the ACCS protein level obtained when the sequence encoding this protein is under the control of various promoters, by using antibodies directed against this protein, as well as the methods described in the section entitled "polypeptides of the invention".

As an embodiment, a non functional regulatory polynucleotide (Pa) comprises a nucleotide sequence extending from nucleotide 1 to nucleotide 3650 of the SEQ ID No 2.

Thus, in the control system according to the present invention, a non functional regulatory polynucleotide (Pa) may comprise a nucleotide sequence extending from nucleotide 1 to nucleotide 3650 of the SEQ ID No 2.

It is a further object of the present invention to provide the hereabove defined regulatory polynucleotide (Pa), per se.

It is a further object of the present invention to provide a nucleic acid comprising the sequence SEQ ID No 2. Such a nucleic acid comprises a regulatory polynucleotide (Pa) and a nucleic acid encoding the ACCS protein of SEQ ID No 3.

A non functional polynucleotide (Pa) may also consist of any polynucleotide derived from the polynucleotide (PA) such as defined hereabove, the nucleotide sequence of which comprises an insertion, a substitution or a deletion of one or more nucleotide(s), as compared to the regulatory polynucleotide nucleotide sequence.

Thus, it is a further object of the present invention to provide a nucleic acid comprising a nucleotide sequence comprising at least one alteration selected from a mutation, an insertion or a deletion, as compared to the nucleic acid extending from nucleotide 1 to nucleotide 5907 of the sequence SEQ ID No 1, the said alteration-containing nucleic acid leading to the reduced expression of the ACCS protein, when it controls the expression of the said protein, as compared to the expression level of the ACCS protein controlled by the nucleic acid extending from nucleotide 1 to nucleotide 5907 of the sequence SEQ ID No 1.

It is a further object of the present invention to provide a control system such as defined hereabove, wherein the regulatory polynucleotide (Pa) is sensitive to the action of an induction signal, and preferably, wherein the regulatory polynucleotide (Pa) is an inducible, transcription or translation-repressing polynucleotide.

As used herein, a "repressing or repressor" regulatory polynucleotide is intended to mean a regulatory sequence which constitutive activity may be blocked by an external signal. Such an external signal may be the lack of binding of a transcription factor recognized by the said repressor regulatory polynucleotide. The lack of binding of the transcription factor may be induced by the action of the repressor induction signal to which the repressor regulatory polynucleotide is sensitive.

In this first particular embodiment, the expression of the sequence encoding an ACCS protein is constitutive in the selected host cell, in the absence of the repressor induction signal to which the repressor regulatory polynucleotide is directly or indirectly sensitive.

Contacting the host cell with the repressor induction signal, by virtue of the direct or indirect action on the repressor regulatory polynucleotide, causes the expression of the polynucleotide encoding the ACCS protein to be inhibited and/or blocked.

To obtain DNA constructs according to the present invention comprising a repressor regulatory polynucleotide, the man skilled in the art will make use of his technical general knowledge in the field of plant gene expression.

A method for producing a transformed plant, implementing this type of regulatory polynucleotide is described in the section entitled "methods for producing a transformed plant of the invention".

Nucleic Acid Encoding a Non Active ACCS Protein

As used herein, a "nucleic acid encoding a non active ACCS protein" is intended to mean a nucleic acid encoding a protein which differs from the ACCS protein of SEQ ID No 3, through a substitution, a deletion, or the insertion of one or more amino acid(s), and which does not possess the biological activity of the ACCS protein of SEQ ID No 3.

Non Active ACCS Protein

As used herein, a "non active ACCS protein" is intended to mean a protein which differs from the ACCS protein of SEQ ID No 3, through a substitution, a deletion, or the insertion of one or more amino acid(s), and which does not possess the biological activity of the ACCS protein of SEQ ID No 3.

In general, a non active ACCS protein is a protein which expression is associated with an andromonoecious or a hermaphroditic phenotype.

As an example, a non active ACCS protein may be a protein which does not allow transforming S-adenosyl methionine to ACC (1-aminocyclopropane-1-carboxylate).

The present inventors have shown in Example 1 that a non active ACCS protein according to the present invention is for example an ACCS protein of SEQ ID No 3 wherein the alanine residue at position 57 is replaced by a valine residue.

Genetic Control Element G/g in the Form of the Recessive Allele (g) of the System of the Invention Generally speaking, the genetic control element (G/g) in the form of the recessive allele (g), when present in a plant, leads to the development of a hermaphroditic or gynoceious plant.

Nucleic Acids of the Invention

As previously mentioned, according to the present invention two allele variants (A) and (a) of a first genetic control element (A/a) were characterized.

The present inventors have identified the nucleic acid of SEQ ID No 1 as being a nucleic acid corresponding to the dominant allele (A) variant and the nucleic acid of SEQ ID No 2, as corresponding to the recessive allele (a) variant, of a first genetic control element in the form of a gene (A/a).

In the control system according to the invention, at least one of both genetic control elements has been artificially inserted into a plant.

As stated hereabove, such an insertion causes the sex of the flower of the plant to change, which is one of the objectives which are sought according to the present invention.

Therefore, sequences SEQ ID No 1 and SEQ ID No 2 are part of the object of the invention.

It is therefore an object of the present invention to provide a nucleic acid comprising a polynucleotide having at least 95% nucleotide identity with a nucleotide sequence selected from SEQ ID No 1 and SEQ ID No 2, or to a fragment of either of SEQ ID No 1 and SEQ ID No 2, provided that such a nucleic acid has the functional characteristics of the allele (A) or of the allele (a) such as defined hereabove.

It is a further object of the present invention to provide a nucleic acid which sequence is complementary to the nucleic acid such as defined hereabove.

It is yet a further object of the present invention to provide a nucleic acid consisting of a polynucleotide having at least 95% nucleotide identity with a sequence selected from SEQ ID No 1 and SEQ ID No 2, or to a fragment of either SEQ ID No 1 or SEQ ID No 2, or a nucleic acid with a sequence complementary thereto, provided that such a nucleic acid has the functional characteristics of the allele (A) or of the allele (a) such as defined hereabove.

The present invention also relates to a nucleic acid comprising at least 12, preferably at least 15 and most preferably at least 20 consecutive nucleotides of the nucleic acid of SEQ ID No 1 or SEQ ID No 2, it being understood that the definition of such a nucleic acid encompasses the "fragments" of a nucleic acid of the invention such as defined in the present description.

The present invention also relates to nucleic acids comprising or consisting of SEQ ID No 1 or 2.

The present invention also relates to a nucleic acid comprising at least 12, preferably at least 15 and most preferably at least 20 consecutive nucleotides of the nucleic acid of SEQ ID No 1 or SEQ ID No 2, it being understood that the definition of such a nucleic acid encompasses the "fragments" of a nucleic acid of the invention such as defined in the present description.

The allele (A) defined by SEQ ID No 1 comprises, from the 5' end to the 3' end, respectively:

a) a non coding sequence comprising elements which regulate the transcription and/or the translation of this gene, located upstream from the first exon, extending from nucleotide at position 1 to nucleotide at position 5906 of the SEQ ID No 1;

b) a so called "coding region" which comprises the three exons and the two introns of the gene (A/a), this coding region extending from nucleotide at position 5907 to nucleotide at position 7915 of the SEQ ID No 1; and c) a non coding region located downstream from the coding region, extending from nucleotide at position 7915 to nucleotide at position 13380 of the SEQ ID No 1.

The allele (a) defined by SEQ ID No 1 comprises, from the 5' end to the 3' end, respectively:

a) a non coding sequence comprising elements which regulate the transcription and/or the translation of this gene, located upstream from the first exon, extending from nucleotide at position 1 to nucleotide at position 3650 of the SEQ ID No 2; which substantially differs from the non coding sequence located at 5' of the nucleic acid of SEQ ID No 1, b) a so called "coding region" which comprises the three exons and the two introns of the gene (A/a), this coding region extending from nucleotide at position 3651 to nucleotide at position 5659 of the SEQ ID No 2 which does not differ much from the coding sequence of the nucleic acid of SEQ ID No 1, and encodes the same ACCS protein of SEQ ID No 3, and c) a non coding region located downstream from the coding region, extending from nucleotide at position 5659 to nucleotide at position 11137 of the SEQ ID No 1, which does not differ much from the non coding sequence located at 3' of the nucleic acid of SEQ ID No 1.

The structural characteristics of the three exons and two introns of the gene A/a are detailed in Table 2 hereunder. The structural characteristics of exons and introns of the alleles (A) and (a) of the gene (A/a) are very similar, so that exons of the alleles (A) and (a) do encode the same protein of SEQ ID No 3. As already stated hereabove, the main difference between the nucleotide sequences corresponding to the alleles (A) and (a) lies in the upstream regulatory sequences corresponding to these two alleles. These two sequences thus have a common region composed of 3 exons and 2 introns, and a non common region comprising distinct regulatory regions.

TABLE 2

Exon sequences in the gene A/a

| Exon # | Nucleotide 5'-position in | | Nucleotide 3'-position in | |
|---|---|---|---|---|
| | SEQ ID N°1 (allele A) | SEQ ID N°2 (Allele a) | SEQ ID N°1 (Allele A) | SEQ ID N°2 (Allele a) |
| 1 | 5907 | 3651 | 6086 | 3830 |
| 2 | 6181 | 3924 | 6467 | 4209 |
| 3 | 7046 | 4790 | 7915 | 5659 |

The present invention further relates to a nucleic acid comprising at least 12 consecutive nucleotides of an exonic polynucleotide of the gene A/a, such as polynucleotides 1 to 3 described in Table 1 hereabove, which are included in the nucleic acid of SEQ ID No 1 and SEQ ID No 2.

Such a nucleic acid encodes at least part of the ACCS protein and may notably be inserted into a recombinant vector intended to express the corresponding translation product in a host cell or in a plant transformed with such recombinant vector, so as to obtain a plant of genotype (A).

Such a nucleic acid may also be used for synthesizing nucleotide probes and primers intended to detect or to amplify nucleotide sequences present in the gene (A/a) in a sample.

If needed, the sequences described hereabove may carry one or more mutation(s), preferably one or more mutation(s) which will induce the synthesis of a non active ACCS protein, and modify the sex type of a plant comprising such a mutated gene (A/a). Such sequences comply with the definition of nucleic acids encoding a non active ACCS protein, such as generally defined hereabove.

TABLE 3

Intron sequences in the gene (A/a)

| Intron # | Nucleotide 5'-position in | | Nucleotide 3'-position in | |
|---|---|---|---|---|
| | SEQ ID N°1 | SEQ ID N°2 | SEQ ID N°1 | SEQ ID N°2 |
| 1 | 6087 | 3831 | 6180 | 3923 |
| 2 | 6468 | 4210 | 7045 | 4789 |

The present invention further relates to a nucleic acid comprising at least 12 consecutive nucleotides of an intron polynucleotide of the gene (A/a), such as polynucleotides 1 and 2 described in Table 2 hereabove, which are included in the nucleic acid of SEQ ID No 1 and SEQ ID NO 2.

Such a nucleic acid may be used as an oligonucleotide probe or primer to detect the presence of at least one copy of the gene (A/a) in a sample, or to amplify a determined target sequence within the gene (A/a).

Such a nucleic acid may also be used to amplify a determined target sequence within the gene (A/a) or to inhibit the same using a sense or a cosuppression approach, or using double stranded RNA (Wassenegger and al. 1996; Kooter and al. 1999) for interference. Such a nucleic acid may also be used for determining functional allele variants of the gene (A/a), which will be used in a method for selecting plants with a determined sex type.

It should be noted that in their common region, i.e. the 3 exons and the 2 introns described hereabove, SEQ ID No 1 and SEQ ID No 2 have a nucleotide identity percentage higher than 95%, this percentage being effectively higher than 99%.

Other Nucleic Acids According to the Invention, Encoding the ACCS Protein

It is a further object of the present invention to provide a nucleic acid comprising a polynucleotide having at least 95% nucleotide identity with the nucleotide sequence starting at nucleotide 5907 and ending at nucleotide 7915 of the SEQ ID No 1 as well as a nucleic acid with a sequence complementary thereto.

The present invention also relates to a nucleic acid having at least 95% nucleotide identity with the nucleotide sequence starting at nucleotide 5907 and ending at nucleotide 7915 of the SEQ ID No 1, as well as a nucleic acid with a sequence complementary thereto.

It is a further object of the present invention to provide a nucleic acid comprising the nucleotide sequence starting at nucleotide 5907 and ending at nucleotide 7915 of the SEQ ID No 1 or a nucleic acid with a sequence complementary thereto.

The present invention further relates to a nucleic acid consisting of the nucleotide sequence starting at nucleotide 5907 and ending at nucleotide 7915 of the SEQ ID No 1 or a nucleic acid with a sequence complementary thereto.

It is yet another object of the present invention to provide a nucleic acid comprising, at least:
(i) one sequence having at least 95% identity with the polynucleotide extending from nucleotide 5907 to nucleotide 6086 of the SEQ ID No 1,
(ii) one sequence having at least 95% identity with the polynucleotide extending from nucleotide 6181 to nucleotide 6467 of the SEQ ID No 1, and
(iii) one sequence having at least 95% identity with the polynucleotide extending from nucleotide 7046 to nucleotide 7915 of the SEQ ID No 1.

It is a further object of the present invention to provide a nucleic acid comprising, from the 5' end to the 3' end:
(i) one sequence extending from nucleotide 5907 to nucleotide 6086 of the SEQ ID No 1,
(ii) one sequence extending from nucleotide 6181 to nucleotide 6467 of the SEQ ID No 1, and
(iii) one sequence extending from nucleotide 7046 to nucleotide 7915 of the SEQ ID No 1.

A nucleic acid encoding the ACCS protein may comprise in addition leader and terminator sequences, that are usual for the man skilled in the art.

Transcription and Translation Products of the Gene (A/a) and Polypeptides of the Invention.

It is therefore another object of the present invention to provide the polypeptide comprising the amino acid sequence SEQ ID No 3, also called "ACCS protein" in the present description, as well as a polypeptide having at least 95% amino acid identity with SEQ ID No 3 or a fragment or a variant thereof.

A fragment of ACCS protein according to the present invention comprises at least 10, 50, 100, 200, 300, 400, 420, 430, 440 or 445 consecutive amino acids of a polypeptide of SEQ ID No 3.

The present invention further relates to a polypeptide comprising an amino acid sequence having at least 95% amino acid identity with the ACCS protein sequence of SEQ ID No 3.

Advantageously, included in the present invention is also a polypeptide having at least 96%, 97%, 98%, 99%, 99.1%, 99.2%, 99.3%, 99.4%, 99.5%, 99.6%, 99.7%, 99.8% or 99.9% amino acid identity with the sequence of a polypeptide of SEQ ID No 3, or a peptide fragment of the latter.

Generally speaking, the polypeptides of the invention may be in an isolated or a purified form.

A polypeptide of the invention may be obtained by genetic recombination using methods that are well known from the man skilled in the art, for example methods described in AUSUBEL and al. (1989).

A polypeptide according to the invention may also be prepared by using conventional methods of chemical synthesis, either in a homogeneous solution or in a solid phase.

Illustratively, a polypeptide of the invention could be prepared by the homogeneous solution method described by HOUBEN WEIL (1974) or by the method of the solid phase synthesis described by MERRIFIELD (1965a; 1965b).

Preferably, the polypeptide variants of a polypeptide according to the invention are still capable of being recognized by antibodies directed against polypeptides of SEQ ID No 3.

A polypeptide encoded by the gene (A/a) according to the invention, such as a polypeptide of amino acid SEQ ID No 3, or a variant or a peptide fragment of the latter, is useful, notably for preparing antibodies intended to detect in a sample the presence and/or the expression of a polypeptide of SEQ ID No 3 or of a peptide fragment of the latter.

It is a further object of the present invention to provide a polypeptide of SEQ ID NO:8 or a polypeptide fragment of this sequence such as defined hereabove. The polypeptide of SEQ ID NO:8 encodes a "non active" ACCS protein according to the 15 definition given hereabove and does differ from the SEQ ID NO:3 by the presence of a valine residue at position 57.

Antibodies directed against these polypeptides not only are used for detecting in a sample the presence of a polypeptide coded by the gene (A/a) or of a peptide fragment of such a polypeptide, but are used also for quantifying the synthesis of a polypeptide of SEQ ID NO: 3 or 8, for example in the cells of a plant, and for so determining the sex of the plant, without necessarily having to culture the said plant.

As used herein "antibodies" are intended to mean notably polyclonal or monoclonal antibodies or fragments (for example F(ab)'$_2$, F(ab) fragments) or any polypeptide comprising a domain of the initial antibody that recognizes the target polypeptide or the target polypeptide fragment according to the invention.

Monoclonal antibodies may be prepared from hybridomas according to the method described by KOHLER and MILSTEIN (1975).

The present invention also relates to antibodies directed against a polypeptide such as described hereabove or a fragment or a variant of the latter, such as produced in the trioma method or in the hybridoma method described by KOZBOR and al. (1983).

The present invention further relates to single chain antibody fragments Fv (ScFv) such as described in the U.S. Pat. No. 4,946,778 or by MARTINEAU and al. (1998).

Antibodies according to the present invention generally encompass antibody fragments obtained from phage banks such as described by RIDDER and al. (1995) or humanized antibodies such as described by REINMANN and al. (1997) and LEGER and al. (1997). Preparations of antibodies according to the present invention are useful in immunological detection tests intended to identify the presence and/or the amount of a polypeptide of SEQ ID No. 3, or of a peptide fragment thereof, present in a sample.

An antibody of the invention may comprise in addition a detectable marker, either isotopic or non isotopic in nature, for example a fluorescent tag, or may be coupled with a molecule such as biotin, using methods that are well known from the man skilled in the art.

Thus, it is a further object of the present invention to provide a method for detecting the presence in a sample of a polypeptide of the invention, said method comprising the steps of:
a) contacting the test sample with an antibody such as described hereabove;
b) detecting the antigen/antibody complex formed.

The present invention further relates to a diagnostic kit for detecting the presence in a sample of a polypeptide of the invention, said kit comprising:
a) an antibody such as defined hereabove;
b) if needed, one or more reagent(s) required for detecting the antigen/antibody complex formed.

It is yet another object of the present invention to provide the use of a nucleic acid or of an allele variant of a nucleic acid such as defined hereabove in plant selection programs for obtaining plants the floral type of which has been modified.

Nucleic Acids Comprising a Functional Regulatory Polynucleotide (PA)

A functional regulatory polynucleotide (PA) or promoter according to the present invention consists in a nucleic acid which allows the ACCS protein of SEQ ID No 3 to be expressed in dicotyledon plants.

Such a functional regulatory polynucleotide (PA) enables thus, when artificially introduced into a plant, to modify the sex of the flowers of such plant, and in particular makes it possible to obtain female plants, that are not capable of self-pollination.

It is therefore also an object of the present invention to provide a nucleic acid comprising a polynucleotide having at least 95% nucleotide identity with the nucleotide sequence starting at nucleotide 1 and ending at nucleotide 5906 of the SEQ ID No 1 as well as a nucleic acid with a sequence complementary thereto.

The present invention also relates to a nucleic acid having at least 95% nucleotide identity with the nucleotide sequence starting at nucleotide 1 and terminating at nucleotide 5906 of the SEQ ID No 1, as well as to a nucleic acid with a complementary sequence.

It is a further object of the present invention to provide a nucleic acid comprising the nucleotide sequence starting at nucleotide 1 and ending at nucleotide 5906 of the SEQ ID No 1 or a nucleic acid with a complementary sequence.

The present invention further relates to a nucleic acid consisting of the nucleotide sequence starting at nucleotide 1 and ending at nucleotide 5906 of the SEQ ID No 1 or to a nucleic acid with a complementary sequence.

The present invention further relates to a nucleic acid comprising at least 12 consecutive nucleotides of a regulatory polynucleotide, such as defined hereabove.

Such a nucleic acid may be used as an oligonucleotide probe or primer to detect the presence in a sample of at least one copy of the allele (A) of the gene (A/a), to amplify a determined target sequence within the gene (A/a). Such a nucleic acid may also be used for seeking functional variant alleles of the gene (A/a), or will be used in a method for selecting plants with a determined sex type.

Detection methods implementing nucleic acids such as described hereabove are described in the section entitled "Selection methods of the invention".

Such a nucleic acid may also be used to inhibit a determined target sequence within the gene (A/a) using an antisense or a cosuppression approach, or using double stranded RNA (Wassenegger and al. 1996; Kooter and al. 1999) for interference.

Nucleic Acids Comprising a Non Functional Regulatory Polynucleotide Pa

A non functional regulatory polynucleotide (Pa) or promoter according to the present invention is a nucleic acid which:
(i) does not allow the expression of the ACCS protein of SEQ ID No 3 in a host cell, or
(ii) allows this protein to be expressed at a very low level as compared to the level observed with the regulatory polynucleotide (PA), or
(iii) allows the ACCS protein to be expressed during the plant life, for a shorter time period, as compared to the expression time period observed with the regulatory polynucleotide (PA).

Such a non functional regulatory polynucleotide (Pa) enables thus, when artificially introduced into a plant, for example when replacing a polynucleotide (A), to modify the flower sex of such plant, and in particular makes it possible to obtain hermaphroditic plants, that are capable of self-pollination.

It is therefore also an object of the present invention to provide a nucleic acid comprising a polynucleotide having at least 95% nucleotide identity with the nucleotide sequence starting at nucleotide 1 and ending at nucleotide 3650 of the SEQ ID No 2 as well as a nucleic acid with a sequence complementary thereto.

The present invention also relates to a nucleic acid having at least 95% nucleotide identity with the nucleotide sequence starting at nucleotide 1 and ending at nucleotide 3650 of the SEQ ID No 2, as well as a nucleic acid with a sequence complementary thereto.

It is a further object of the present invention to provide a nucleic acid comprising the nucleotide sequence starting at nucleotide 1 and ending at nucleotide 3650 of the SEQ ID No 2 or a nucleic acid with a sequence complementary thereto.

The present invention further relates to a nucleic acid consisting of the nucleotide sequence starting at nucleotide 1 and ending at nucleotide 3650 of the SEQ ID No 2 or to a nucleic acid with a sequence complementary thereto.

Such a nucleic acid may be used as an oligonucleotide probe or primer to detect the presence in a sample of at least one copy of the allele (a) of the gene (A/a), or to amplify a determined target sequence within the gene (A/a).

The present invention also relates to nucleic acids comprising a combination of one or more nucleic acid(s) such as defined hereabove, for example a nucleic acid encoding a functional ACCS protein under the control of a promoter of the (PA) or (Pa) type.

General Definitions

According to the invention, any usual method of molecular biology, microbiology and DNA recombination known from the man skilled in the art may be used. Such methods are described for example by SAMBROOK and al. (1989), GLOVER (1985), GAIT (1984), HAMES and HIGGINS (1984), BERBAL (1984) and AUSUBEL and al. (1994).

Preferably, any nucleic acid and any polypeptide of the invention is present in an isolated or a purified form.

As used herein, "isolated" is intended to mean a biological material which was removed from its original environment (i.e. the environment wherein it is naturally located). For example, a polynucleotide that is naturally present in a plant is not isolated. The same polynucleotide, separated from adjacent nucleic acids within which it is naturally inserted in the genome of the plant, is isolated. Such a polynucleotide may be introduced into a vector and/or such a polynucleotide may be incorporated into a composition while remaining in an isolated state since the vector or the composition is not its natural environment.

As used herein, "purified" does not require the material be present in an absolutely purified form, excluding the presence of other compounds. It should rather be interpreted as a relative definition.

A polynucleotide or a polypeptide is in a purified state after purification of the raw material or of the natural material of at least one order of magnitude, preferably at least 2 or 3 and preferably at least four or five orders of magnitude.

For the purpose of the present description, a "nucleotide sequence" is intended to mean either a polynucleotide or a nucleic acid. A "nucleotide sequence" includes the genetic material itself and thus is not limited to the only information about the sequence thereof.

A "nucleic acid", a "polynucleotide", an "oligonucleotide" or a "nucleotide sequence" encompass RNA, DNA, cDNA sequences or RNA/DNA hybrid sequences of more than one nucleotide, either in a single or in a double stranded form.

As used herein, a "nucleotide" is intended to mean both natural nucleotides (A, T, G, C) and modified nucleotides which comprise at least one modification such as (i) a purine analogue, (ii) a pyrimidine analogue, or (iii) a sugar analogue, such modified nucleotides being described for example in the PCT application WO 95/04064.

For the purpose of the present invention, a first polynucleotide is considered as being "complementary" to a second polynucleotide when each base of the first polynucleotide is paired with the complementary base of the second polynucleotide which has a reverse orientation. Complementary bases are A and T (or A and U), and C and G.

According to the invention, a first nucleic acid having at least 95% identity with a second reference nucleic acid, will have at least 95%, preferably at least 96%, 97%, 98%, 98.5%, 99%, 99.1%, 99.2%, 99.3%, 99.4%, 99.5%, 99.6%, 99.7%, 99.8% or 99.9% nucleotide identity with this second reference polynucleotide, the percentage of identity between two sequences being determined as described hereunder.

As used herein, the said "percentage of identity" between two nucleic acid sequences is determined by comparing the two optimally aligned sequences, through a comparison window.

The portion of the nucleotide sequence within the comparison window may thus comprise additions or deletions (for example gaps) as compared to the reference sequence (which does not comprise these additions or deletions) so as to obtain an optimal alignment between the two sequences.

The percentage of identity is calculated by determining the number of positions at which an identical nucleic base is observed for the two compared sequences, then by dividing the number of positions where there is an identity between the two nucleic bases by the total number of positions within the comparison window, lastly by multiplying the result by hundred to obtain the identity percentage of nucleotides for both sequences.

An optimal sequence alignment for comparison may be calculated by computer programs using known algorithms.

Most preferably, said sequence identity percentage is determined using the CLUSTAL W software (version 1.82) which parameters are set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

A nucleic acid having at least 95% nucleotide identity with a nucleic acid of the invention encompasses said "variants" of a nucleic acid of the invention.

As used herein, a nucleic acid "variant" of the invention is intended to mean a nucleic acid which differs from the reference nucleic acid through one or more substitution(s), addition(s) or deletion(s) of a nucleotide, as compared to the reference nucleic acid. A nucleic acid variant of the invention may be of natural origin, such as an allele variant which is naturally present in nature. Such a variant nucleic acid may also be a non natural nucleic acid obtained, for example, by mutagenesis methods.

Differences between the reference nucleic acid and the "variant" nucleic acid are generally minor so that the reference nucleic acid and the variant nucleic acid do possess very similar nucleotide sequences, that are even the same in many regions. The nucleotide mutations that do occur in a variant nucleic acid may be silent mutations, that is to say mutations which do not affect the amino acid sequence which may be coded by this variant nucleic acid.

Nucleotide changes in the variant nucleic acid may also lead to substitutions, additions or deletions of one or more amino acid(s) in the sequence of the polypeptide which may be coded by this variant nucleic acid.

Most preferably, a variant nucleic acid of the present invention comprising an open reading frame, encodes a polypeptide which retains the same biological function or activity as the polypeptide coded by the reference nucleic acid.

Most preferably, a variant nucleic acid of the present invention which comprises an open reading frame, encodes a polypeptide which remains capable of being recognized by antibodies directed against the polypeptide coded by the reference nucleic acid.

Said "variants" of a nucleic acid encoding the ACCS protein encompass nucleic acids of ACCS protein orthologous genes introduced into the genome of the plants, and possessing a nucleotide identity of at least 95% with a nucleic acid encoding ACCS protein.

As used herein, a "fragment" of a nucleic acid of the invention is intended to mean a nucleotide sequence with a reduced length as compared to that of the reference nucleic acid, the nucleic acid fragment possessing the same nucleotide sequence as the reference nucleic acid on the common part thereof. Such fragments of a nucleic acid of the invention have at least 12, 15, 18, 20, 25, 30, 35, 40, 45, 50, 60, 70, 80, 90, 100, 150, 200, 300, 400, 500, 1000, 2000 or 3000 consecutive nucleotides of the reference nucleic acid, where the maximum nucleotide length for a fragment of a nucleic acid of the invention being of course limited by the maximum nucleotide length of the reference nucleic acid.

Probes and Primers

The nucleic acids of the invention, and in particular the SEQ ID No 1 and SEQ ID $NO_2$, their fragments of at least 12 nucleotides, the regulatory polynucleotides (PA) and (Pa), as well as nucleic acids with a complementary sequence, are useful for detecting the presence in a sample of at least one copy of a nucleotide sequence of the gene (A/a) or of a fragment or of an allele variant thereof.

In particular, the hereabove probes and primers derived from SEQ ID No 1, and in particular derived from the regulatory polynucleotide (PA) may be used for detecting the presence of the allele (A) in a dicotyledon plant.

Likewise, the hereabove probes and primers derived from SEQ ID No 2, and in particular derived from the non functional regulatory polynucleotide (Pa) may be used for detecting the presence of the allele (a) in a dicotyledon plant.

Also encompassed by the present invention are nucleotide probes and primers hybridizing, under strongly stringent hybridization conditions, with a nucleic acid selected from SEQ ID No 1 and SEQ ID No 2, or with a regulatory polynucleotide (PA) or (Pa).

It is therefore also an object of the present invention to provide a nucleic acid, to be used as a probe or a primer, specifically hybridizing with a nucleic acid such as defined hereabove.

The hereunder mentioned hybridization conditions are implemented for hybridizing a 20 base-long nucleic acid, probe or primer.

The hybridization degree and specificity depend on various parameters, such as:

a) the purity of the nucleic acid preparation with which the probe or the primer shall hybridize;

b) the base composition of the probe or the primer, G-C base pairs possessing a higher thermal stability than A-T or A-U base pairs;

c) the length of the homologous base sequence between the probe or the primer and the nucleic acid;

d) the ionic strength: the hybridization level does increase as the ionic strength and the incubation period do increase;

e) the incubation temperature;

f) the concentration of the nucleic acid with which the probe or the primer shall hybridize;

g) the presence of decharacterizing agents such as agents promoting the hydrogen bond rupture, like formamide or urea, which increase the hybridization stringency;

h) the incubation times, the hybridization level increasing with the incubation period;

i) the presence of volume exclusion agents, such as dextran or dextran sulfate, which increase the hybridization level because they increase in the preparation the effective concentrations of the probe or the primer and of the nucleic acid which shall hybridize therewith.

The parameters which define the stringency conditions depend on the temperature at which 50% of paired strands do separate (Tm).

For sequences comprising more than 360 bases, Tm is defined by the following relationship:

Tm=81.5+0.41(% G+C)+16.6 Log(cation concentration)−0.63 (% formamide)−(600/base number) (SAMBROOK AND al., (1989), pages 9.54-9.62).

For sequences of less than 30 base-length, Tm is defined by the following relationship: Tm=4(G+C)+2(A+T).

Under suitable stringency conditions, where a specific sequences will not hybridize, the hybridization temperature approximately ranges from 5 to 30° C., preferably from 5 to 10° C. below Tm.

As used herein, said "strongly stringent hybridization conditions" according to the invention mean hybridization conditions such as with a hybridization temperature of 5° C. below Tm.

The hereabove described hybridization conditions may be adapted depending on the length and on the base composition of the nucleic acid which hybridization is sought for or on the chosen labelling type, according to methods known from the man skilled in the art.

Suitable hybridization conditions may be for example adapted according to the learnings from the book written by HAMES and HIGGINS (1985) or by AUSUBEL and al. (1989).

As an illustration, hybridization conditions used for a 200 base-long nucleic acid are as follows:

Prehybridization:
The same conditions as for hybridization
time: 1 night.

Hybridization:
5×SSPE (0.9 M NaCl, 50 mM sodium phosphate pH 7.7, 5 mM EDTA)
5×Denhardt's (0.2% PVP, 0.2% Ficoll, 0.2% SAB)
100 µg/ml salmon sperm DNA
0.1% SDS
time: 1 night.

Washings:
2×SSC, 0.1% SDS 10 min 65° C.
1×SSC, 0.1% SDS 10 min 65° C.
0.5×SSC, 0.1% SDS 10 min 65° C.
0.1×SSC, 0.1% SDS 10 min 65° C.

The nucleotide probes and primers of the invention comprise at least 12 consecutive nucleotides of a nucleic acid of the invention, in particular of a nucleic acid of SEQ ID No 1 or SEQ ID No 2 or of the sequence complementary thereto, of a nucleic acid having 95% nucleotide identity with a sequence selected from SEQ ID No 1 or 2, or of the sequence complementary thereto, or of a nucleic acid hybridizing under strongly stringent hybridization conditions with a sequence selected from SEQ ID No 1 or 2 or of the sequence complementary thereto.

Preferably, the nucleotide probes and primers according to the invention will have a length of at least 12, 15, 18, 20, 25, 30, 35, 40, 45, 50, 60, 100, 150, 200, 300, 400, 500, 1000, 2000 or 3000 consecutive nucleotides of a nucleic acid of the invention.

Alternatively, a nucleotide probe or primer according to the present invention will consist and/or comprise fragments with a length of 12, 15, 18, 20, 25, 30, 35, 40, 45, 50, 60, 100, 150, 200, 300, 400, 500, 1000, 2000 or 3000 consecutive nucleotides of a nucleic acid of the invention.

As an example, the pair of primers defined by SEQ ID NO: 5, corresponding to a sense primer, and by SEQ ID NO: 6, corresponding to an antisense primer, enables to amplify a nucleic acid fragment of SEQ ID NO: 1 or a nucleic acid fragment of SEQ ID NO: 2.

A nucleotide probe or primer according to the present invention may be prepared by any suitable method well known from the man skilled in the art, including by cloning and use of restriction enzymes or by a direct chemical synthesis according to methods such as the phosphodiester method from NARANG and al. (1979) or from BROWN and al. (1979), the diethyl phosphoramidite method from BEAUCAGE and al. (1980) or the method on a solid support described in the European patent no EP 0 707 592. Each of the nucleic acids of the invention, including the hereabove described oligonucleotide probes and primers, may be labeled, if desired, by incorporating a detectable molecule, that is to say a detectable marker, by spectroscopic, photochemical, biochemical, immunochemical or chemical means.

For example, such markers may consist in radioactive isotopes ($^{32}P$ $^{3}H$, $^{35}S$), fluorescent molecules (5-bromodeoxyuridine, fluorescein, acetyl aminofluorene) or ligands such as biotin.

Probe labelling is preferably effected by inserting labeled molecules into the polynucleotides by primer extension or by addition to the 5' or 3' ends.

Examples of nucleic acid fragment non radioactive labelling are especially described in the French patent no FR 78 10 975 or in articles written by URDEA and al. (1988) or by SANCHEZ PESCADOR and al. (1988).

Advantageously, the probes according to the present invention may have structural characteristics making it possible due to their nature to amplify the signal, such as probes described by URDEA and al; (1991) or in the European patent no EP 0 225 807 (Chiron).

The oligonucleotide probes of the invention may be used especially in hybridizations of the Southern type with any nucleic acid encoding ACCS protein, and in particular nucleic acids of SEQ ID No 1 or 2, or in RNA-hybridizations when the expression of the corresponding transcript is to be analyzed in a sample.

The probes of the invention may also be used for detecting PCR amplification products or for detecting any mispairing.

Nucleotide probes and primers of the invention may be fixed on a solid support. Such solid supports are well known from the man skilled in the art and include the well surfaces of microtiter plates, polystyrene flakes, magnetic beads, nitrocellulose strips or microparticles such as latex particles.

Therefore, it is a further object of the present invention to provide a nucleic acid to be used as a nucleotide probe or primer characterized in that it comprises at least 12 consecutive nucleotides of a nucleic acid such as defined hereabove, in particular of a nucleic acid of SEQ ID No 1 and SEQ ID No 2.

The present invention further relates to a nucleic acid to be used as a nucleotide probe or primer characterized in that it consists in a polynucleotide of at least 12 consecutive nucleotides of a nucleic acid of the invention, most preferably of a nucleic acid with sequences selected from SEQ ID No 1 and SEQ ID No 2.

As described hereabove, such a nucleic acid may in addition be characterized in that it is labeled using a detectable molecule.

A nucleic acid to be used as a nucleotide probe or primer for detecting or amplifying a genomic sequence, mRNA or cDNA of the gene (A/a) may in addition be characterized in that it is selected from the following sequences:

a) the nucleotide sequences hybridizing, under strongly stringent hybridization conditions, with a nucleic acid of SEQ ID No 1 or SEQ ID No 2; and b) the sequences comprising at least 12 consecutive nucleotides of a nucleic acid of SEQ ID No 1 or SEQ ID No 2.

Vectors, Cells and Plants of the Invention

In the control system according to the invention, to ensure that at least one of the genetic control elements is artificially inserted into the dicotyledon plant, the hereabove defined nucleic acids and regulatory polynucleotides should be introduced into vectors, then into cells.

Thus, it is a further object of the present invention to provide vectors, cells and transformed plants, which comprise the regulatory polynucleotides (PA) and (Pa), nucleic acids encoding active and non active proteins ACCS, as well as nucleic acids corresponding to the alleles (G) and (g) such as described hereabove, and the hereabove defined primers.

Vectors

A nucleic acid such as defined hereabove, thereafter called "nucleic acid of interest", may be inserted into a suitable vector.

As used herein, a "vector" is intended to mean a DNA or RNA circular or linear molecule which may be either single stranded or double stranded.

A recombinant vector according to the present invention is preferably an expression vector, or more specifically an insertion vector, a transformation vector or an integration vector.

It may be especially a vector of bacterial or viral origin.

In any case, the nucleic acid of interest is placed under the control of one or more sequence(s) comprising signals for regulating its expression in the considered plant, and either regulatory signals are all comprised in the nucleic acid of interest, as is the case in the nucleic acid constructs described in the previous section, or one, many of them or all regulatory signals are comprised in the receiving vector into which the nucleic acid of interest has been inserted.

A recombinant vector of the invention advantageously comprises suitable transcription start and stop sequences.

Moreover, the recombinant vectors of the invention may include one or more functional replication origins in the host cells where their expression is expected, as well as, if needed, nucleotide sequences that are markers for selection.

The recombinant vectors of the invention may also include one or more of the expression regulatory signal(s) defined hereabove in the description.

Preferred bacterial vectors according to the present invention include for example vectors pBR322 (ATCC no 37 017) or vectors such as pAA223-3 (Pharmacia, Uppsala, Sweden) and pGEM1 (Promega Biotech, Madison, Wis., United States).

Other commercial vectors may also be mentioned such as vectors pQE70, pQE60, pQE9 (Quiagen), psiX174, pBluescript SA, pNH8A, pMH16A, pMH18A, pMH46A, pWLNEO, pSV2CAT, pOG44, pXTI and pSG (Stratagene).

It may also be vectors of the Baculovirus type such as the vector pVL1392/1393 (Pharmingen) used to transfect the cells of the Sf9 line (ATCC No C . . . RL 1711) derived from *Spodoptera frugiperda*.

Preferably, and for the main application of the vectors of the invention aiming at producing a stable and preferably inducible expression, of a sequence encoding an ACCS protein in a plant, vectors will be used, that are especially adapted to the expression of interesting sequences in plant cells, such as the following vectors:

vector pBIN19 (BEVAN and al.), marketed by the CLONTECH company (Palo Alto, Calif., USA);

vector pBI 101 (JEFFERSON, 1987), marketed by the CLONTECH company;

vector pBI121 (JEFFERSON, 1987), marketed by the CLONTECH company;

vector pEGFP; Yang and al. (1996), marketed by the CLONTECH company;

vector pCAMBIA 1302 (HAJDUKIIEWICZ and al., 1994)

intermediate and super-binary vectors derived from vectors pSB12 and pSB1 described by Japan Tobacco (EP 672 752 and Ishida and al., 1996).

As an example, in the control system according to the invention, the gene (A/a), in the form of the allele (A), may be artificially introduced into the dicotyledon plant by using the nucleic acid of SEQ ID NO: 7, which comprises, from the 5' end to the 3' end:

part of the sequence of a vector pEC2, located between nucleotide at position 1 and nucleotide at position 633 of the SEQ ID NO: 7, the sequence of the NotI restriction site, located between nucleotide at position 634 and nucleotide at position 641 of the SEQ ID NO: 7, the sequence of a nucleic acid comprising the gene (A/a), in the form of the allele (A), located between nucleotide at position 642 and nucleotide at position 14020 of the SEQ ID NO: 7, the sequence of the NotI restriction site, located between nucleotide at position 14021 and nucleotide at position 14028 of the SEQ ID NO: 7, part of the sequence of a vector pEC2, located between nucleotide at position 14029 to nucleotide at position 16177 of the SEQ ID NO: 7.

Thus, SEQ ID NO: 7 comprises a linearized vector pEC2, into which the sequence of a nucleic acid comprising the gene (A/a), in the form of the allele (A) has been inserted, by using the NotI restriction site of the vector.

Cells

The most widely used methods for introducing nucleic acids into bacterial cells may be used in the frame of the present invention, i.e. by the fusion of receptor cells with DNA-comprising bacterial protoplasts, by electroporation, by bombardment with projectiles, by viral vector-mediated infection, etc. Bacterial cells are often used to amplify the number of plasmids comprising the construct having the nucleotide sequence according to the invention. Bacteria are cultured and plasmids are then isolated using methods that are well known from the man skilled in the art (see the already mentioned procedure manuals), including the commercially available plasmid purification kits such as for example EasyPrepl from Pharmacia Biotech or QIAexpress Expression System from Qiagen. The thus isolated and purified plasmids are then manipulated to produce other plasmids which will be used to transfect the plant cells.

To ensure the expression of a nucleic acid of interest according to the present invention placed under the control of a suitable regulatory sequence, the nucleic acids or the recombinant vectors defined in the present description shall be introduced into a host cell. The introduction of the polynucleotides according to the present invention into a host cell may be conducted in vitro, according to methods well known from the man skilled in the art.

It is a further object of the present invention to provide a host cell transformed with a nucleic acid of the invention or with a recombinant vector such as defined hereabove.

The origin of such a transformed host cell is preferably a bacterial, fungal or vegetable origin.

Thus, bacterial cells derived from various *Escherichia Coli* strains or from *agrobacterium tumefaciens* strains may be especially used Advantageously, the transformed host cell is a plant cell or a plant protoplast.

Cells that may be transformed according to the method of the invention include for example cells of dicotyledon plants, preferably belonging to the cucurbitaceae family, the members of which are detailed hereunder in the section entitled "plants of the invention".

The hybrid plants obtained by cross-breeding plants of the invention, are also included within the scope of the invention.

Preferably, it is a cell or a protoplast of a plant belonging to the *cucumis melo* species.

It is a further object of the present invention to provide the use of an interesting nucleic acid, for producing a transformed plant which sex phenotype was modified.

The present invention further relates to the use of a recombinant vector such as defined in the present description for producing a transformed plant which sex phenotype was modified.

The present invention also relates to the use of a host cell transformed with an interesting nucleic acid, for producing a transformed plant which sex phenotype was modified.

The present invention also relates to a transformed plant comprising a plurality of host cells such as defined hereabove.

Transformed Plants of the Invention

The present invention also relates to a transformed plant multicellular cell organism, characterized in that it comprises a transformed host cell or a plurality of host cells transformed by at least one of the hereabove defined nucleic acids or by a recombinant vector comprising such a nucleic acid.

The transformed plant may comprise a plurality of copies of a nucleic acid encoding ACCS protein, in such situations where an ACCS protein overexpression is sought. An ACCS protein overexpression is especially sought for when plants producing female flowers, non able to self-pollinate, are expected.

The present invention thus also relates to a transformed plant such as defined hereabove which flowers are exclusively female or hermaphroditic flowers.

The transformed plants of the invention all comprise at least one element selected from nucleic acids and the hereabove defined regulatory polynucleotides that were artificially inserted into their genome.

Hybrid plants obtained by cross-breeding transformed plants of the invention are also encompassed within the scope of the invention.

The present invention also relates to any part of a transformed plant such as defined in the present description, such as the root, but also the aerial parts like the stem, leaves, the flower and above all the seed or the fruit.

It is a further object of the present invention to provide seeds or a plant seed produced by a transformed plant such as defined hereabove.

Typically, such a transformed seed or grain comprises one or more cell(s) comprising in their genome one or more copy or copies of the first and second genetic control elements such as defined hereabove, artificially introduced into said dicotyledon plant enabling to synthesize an ACCS protein at a high amount level or at a low amount level optionally in a controlled and inducible manner.

In a preferred embodiment of a transformed plant of the invention, ACCS protein is to be expressed in a controlled manner, which involves that the transformed plant does only comprise as a functional copy of a polynucleotide encoding ACCS protein, the copy or copies which was or were artificially introduced into cells thereof, and preferably into their genome, while the sequences of the gene (A/a) encoding ACCS, that are naturally present in a wild plant do carry at least one mutation causing a defective expression of the gene (A/a).

The transformed plants according to the present invention are dicotyledons, preferably belonging to the cucurbitaceae family, and in particular to the genus selected from:

*Abobra, Acanthosicyos, Actinostemma, Alsomitra, Ampelosicyos, Anacaona, Apat3ingania, Apodanthera, Bambekea, Benincasa, Biswarea, Bolbostemma, Brandegea, bryonia, Calycophysum, Cayaponia, Cephalopentandra, Ceratosanthes, Chalema, Cionosicyos, Citrullus, Coccinia, Cogniauxia, Corallocarpus, Cremastopus, Ctenolepis, Cucumella, Cucumeropsis, Cucumis, Cucurbita, Cucurbitella, Cyclanthera, Cyclantheropsis, Dactyliandra, Dendrosicyos, Dicoelospermum, Dieterlea, Diplocyclos, Doyerea, Ecballium, Echinocystis, Echinopepon, Edgaria, Elateriopsis, Eureiandra, Fevillea, Gerrardanthus, Gomphogyne, Gurania, Guraniopsis, Gymnopetalum, Gynostemma, Halosicyos, Hanburia, Helmontia, Hemsleya, Herpetospermum, Hodgsonia, Ibervillea, Indofevillea, Kedrostis, Lagenaria, Lemurosicyos, Luffa, Marah, Melancium, Melothria, Melothrianthus, Microsechium, Momordica, Muellerargia, Mukia, Myrmecosicyos, Neoalsomitra, Nothoalsomitra, Odosicyos, Oreosyce, Parasicyos, Penelopeia, Peponium, Peponopsis, Polyclathra, Posadaea, Praecitrullus, Pseudocyclanthera, Pseudosicydium, Psiguria, Pteropepon, Pterosicyos, Raphidiocystis, Ruthalicia, Rytidostylis, Schizocarpum, Schizopepon, Sechiopsis, Sechium, Selysia, Seyrigia, Sicana, Sicydium, Sicyos, Sicyosperma, Siolmatra, Siraitia, Solena, Tecunumania, Telfairia, Thladiantha, Trichosanthes, Tricyclandra, Trochomeria, Trochomeriopsis, Tumamoca, Vaseyanthus, Wilbrandia, Xerosicyos, zanonia, zehneria, zombitsia,* or *zygosicyos.*

Preferably, the transformed plants belong to the *cucumis* genus and to the *cucumis melo* species.

Detection Methods of the Invention

The fact that the present inventors identified the floral development control system made it possible to develop very simple methods for detecting the sex phenotype of the plants, which methods will be detailed hereunder.

A method for detecting the presence of an allele (A) or (a), the said method comprising the following steps of:

1) bringing into contact a nucleotide probe or a plurality of nucleotide probes such as defined hereabove with the test sample; and 2) detecting the complex eventually formed between the probe(s) and the nucleic acid present in the sample.

A method for detecting the presence of an allele (G) or (g), the said method comprising the steps of:

1) bringing into contact a nucleotide probe or a plurality of nucleotide probes such as defined hereabove with the test sample; and
2) detecting the complex eventually formed between the probe(s) and the nucleic acid present in the sample.

Both detection methods enable selecting plants the phenotypes and genotypes of which are summarized in Table 1.

Detecting the complex formed between a nucleic acid and a probe may be performed using any method known from the man skilled in the art, and in particular by using labeled probes or primers, such as described in the section "Probes and primers of the invention".

Such methods are particularly advantageous because they make it unnecessary to culture a dicotyledon plant to know the sex phenotype thereof. It then becomes possible to economically detect the sex phenotype from a very large plant sampling.

Moreover, such methods enable to select late expression phenotypic characters such as the emergence of the flower sex phenotype on plants at a very early development stage (plantlet with the first leaves). The hereabove mentioned application enables to save a considerable amount of time and space.

The present inventors have shown (example 1) that the allele (A) and the allele (a) are associated with a single nucleotide polymorphism (SNP). Thus, the allele (A) of SEQ ID n° 1 comprises, from position 6074 to position 6077, one sequence AGCT, that does result in the presence of an alanine residue at position 54 in ACCS protein of SEQ ID No 3. The allele (a) of SEQ ID n° 2 comprises, from position 3817 to position 3820, one sequence AGTT, that does result in the presence of a valine residue at position 54 in ACCS protein.

The present inventors have shown that amongst both sequences identified hereabove, only the sequence AGCT at position 6074 to 6077 of the SEQ ID N° 1 corresponding to the allele (A) and having a cytosine residue at position 6076 represents a restriction site for the Alu I enzyme. Therefore, the digestion method using the so called "Cleaved Amplified Polymorphic Sequence Markers" (CAPS) known from the man skilled in the art may be used to identify the presence in a plant of the allele (A) or of the allele (a).

In this method, a PCR amplification step is conducted, by using a couple of particular primers satisfying to the following criteria:

the pair of primers does flank the SNP region,
the pair of primers does enable to amplify the allele (A) and the allele (a),
the pair of primers does enable to observe after the Alu I-mediated enzymatic digestion a number of restriction fragments that are different depending on whether the allele (A) or the allele (a) has been amplified.

As an example, such a pair of primers comprises SEQ ID NO: 9 and SEQ ID NO: 10.

In a second step, the products resulting from the PCR are contacted with the restriction enzyme Alu I, under conditions suitable for cleavage.

The thus enzymatically digested or non digested products resulting from the PCR, depending on their nucleotide sequence are thereafter discriminated using traditional methods, for example based on their size.

By applying this method, the man skilled in the art can easily distinguish between a plant comprising the allele (A) and a plant comprising the allele (a) since the PCR products derived from a plant comprising the allele (A) will be digested by the restriction enzyme at the SNP level. These PCR products will be easily distinguished from the PCR products derived from a plant comprising the allele (a), non digested by the restriction enzyme at the SNP level.

It is therefore also an object of the present invention to provide a method for detecting the presence of an allele (A) or (a), said method comprising the following steps of:

PCR amplifying DNA in a sample to be analyzed by using primers of SEQ ID No 11 and SEQ ID No 12,
digesting by the restriction enzyme Alu I the resulting product, and
detecting the resulting restriction fragments.

To detect the resulting restriction fragments, the man skilled in the art will perform an electrophoresis for example in order to detect the fragments depending on their size.

For plants comprising the allele (A), 4 restriction fragments are obtained. Their size is respectively 327, 197, 137 and 116 pb.

For plants comprising the allele (a), 3 restriction fragments are obtained, Their size is respectively 524, 137 and 116 pb.

Such method therefore enables to easily detect the sex phenotype of a plant.

Selection Methods of the Invention

The hereabove detection methods may be implemented in the selection methods that are detailed hereunder.

It is an object of the present invention to provide a method for selecting the floral type of a plant belonging to the cucurbitaceae genus, characterized in that it comprises the following steps:

a) determining the presence of the alleles (A) and (a), in a plant of interest belonging to the cucurbitaceae family, for example by using the nucleic acids such as defined hereabove, or an antibody directed against the ACCS protein and
b) selecting positively the plant which comprises the allele (A) or the allele (a) within its genome.

It is a further object of the present invention to provide a method for selecting the floral type of a plant belonging to the cucurbitaceae genus, characterized in that it comprises a step consisting in:

a) determining the presence of the alleles (G) and (g), in a plant of interest belonging to the cucurbitaceae family, for example by using the nucleic acids such as defined hereabove, and
b) selecting positively the plant which comprises the allele (G) or the allele (g) within its genome.

Determining the presence of the alleles (A), (a), (G) and (g) may be advantageously performed by implementing the hereabove detection methods.

The man skilled in the art may easily combine the selection methods defined hereabove, by referring to Table 1, illustrating the relation that exists between genotype and phenotype, to obtain plants having exclusively a female or an hermaphroditic phenotype, for example.

Methods for Producing a Transformed Plant of the Invention

The present invention relates first to a method for producing a transformed plant aiming at inserting the allele (A) into a plant devoid of this allele.

It is therefore an object of the present invention to provide a method for producing a transformed plant, belonging to the cucurbitaceae family, comprising female flowers, characterized in that it comprises the following steps of:

a) transforming at least one plant cell of a plant of interest that does not comprise the allele (A), within its genome, with a nucleotide sequence (NA); or a recombinant vector comprising such a nucleic acid,
b) selecting the transformed cells obtained in step a) with the nucleic acid (NA) integrated in their genome, c) regenerating a transformed plant from the transformed cells obtained in step b).

This type of method is particularly useful as it makes possible inserting the allele (A) into the genome of a plant, which will thus have a monoecious or gynoic phenotype.

It is a further object of the present invention to provide a method for transforming plants aiming at removing the allele (A) in a plant, or at replacing the allele (A) with an allele (a) so as to obtain a plant with a bisexual phenotype.

It is therefore an object of the present invention to provide a method for producing a transformed plant, belonging to the cucurbitaceae family, having hermaphoroditic flowers, characterized in that it comprises the following steps of:

a) replacing the allele (A) by an allele (a) in a plant, b) selecting the transformed cells obtained in step a) that have integrated in their genome the allele (a), c) regenerating a transformed plant from the transformed cells obtained in step b), d) cross-breeding the plants obtained in step c) to obtain a plant that does not comprise an allele (A) anymore.

In a first embodiment of the hereabove method, step a) does consist of transforming a plant comprising the allele (A) within its genome, with a nucleic acid of the "antisense" type such as defined hereabove, and by selecting the plants that do not comprise the allele (A) anymore.

The same result may be obtained by using homologous recombination techniques aiming at replacing all or part of the nucleic acid (NA) with a nucleic acid having an impaired structure, which does not enable to obtain a phenotype corresponding to the allele (A).

This nucleic acid having an impaired structure may be a regulatory polynucleotide (Pa) or a nucleic acid encoding an altered ACCS protein.

It is therefore an object of the present invention to provide a method for producing a transformed plant, belonging to the cucurbitaceae family, having hermaphroditic flowers, characterized in that it comprises the following steps of:

a) transforming at least one vegetable cell of a plant of interest comprising an allele (A), with a regulatory polynucleotide (Pa) or with a nucleic acid encoding an altered ACCS protein; or a recombinant vector comprising such a nucleic acid, b) selecting the transformed cells obtained in step a) that have at least one copy of a regulatory polynucleotide (Pa) or a nucleic acid encoding an altered ACCS protein integrated in their genome, c) regenerating a transformed plant from the transformed cells obtained in step b), d) cross-breeding the plants obtained in step c) to obtain a plant that does not comprise any allele (A) anymore.

This type of method is particularly useful as it makes it possible to obtain plants that do not comprise any allele (A) anymore, and which are of the andromonoecious or the hermaphroditic type.

The present invention also relates to a method for transforming plants aiming at inserting the allele (G).

It is therefore an object of the present invention to provide a method for producing a transformed plant, belonging to the cucurbitaceae family, comprising female flowers, characterized in that it comprises the following steps of:

a) transforming at least one vegetable cell of a plant of interest that does not comprise the allele (G), within its genome, with a nucleotide sequence (NG); or a recombinant vector comprising such a nucleic acid, b) selecting the transformed cells obtained in step a) having the nucleic acid (NG) integrated in their genome, c) regenerating a transformed plant from the transformed cells obtained in step b).

The present invention also relates to a method for transforming plants aiming at replacing the allele (G) with the allele (g).

It is therefore an object of the present invention to provide a method for producing a transformed plant, belonging to the cucurbitaceae family, having hermaphroditic flowers, characterized in that it comprises the following steps of:

a) replacing the allele (G) with an allele (g) in a plant, b) selecting the transformed cells obtained in step a) that have the allele (g) integrated in their genome, c) regenerating a transformed plant from the transformed cells obtained in step b), d) cross-breeding the plants obtained in step c) to obtain a plant that does not comprise any allele (G) anymore.

The hereabove methods may be combined with each other by relying on Table 1, so as to obtain plants that are exclusively female or exclusively hermaphroditic, the industrial interest of which has been previously discussed.

To simplify the methods for producing an exclusively female or an exclusively hermaphroditic transformed plant, it may be contemplated to conduct a prior step in the hereabove defined methods, during which mutations of the genes (A/a) and (G/g) naturally present in the plant will be performed, for example by randomly inserting the transposon Mutator into a plant population having a wild type phenotype, then by detecting amongst the resulting mutants, those which are of the genotype (aagg), for example using the nucleotide probes or primers described in the examples.

In this preferred embodiment, the transformed plant of the invention is characterized in that it comprises a genotype (aagg) and has flowers that are exclusively hermaphroditic.

In an embodiment of the methods for producing a transformed plant as defined hereabove, the polynucleotide (NA), when used, comprises an inducible activating regulatory polynucleotide (PA).

It is therefore also an object of the present invention to provide a method for producing plant seeds which upon development do produce plants with female flowers, comprising the following steps of:

a) culturing an interesting plant that does not comprise the allele (A) such as defined above within its genome, transformed with a nucleotide sequence (NA) comprising an inducible activating regulatory polynucleotide (PA); or with a recombinant vector comprising this nucleic acid;

in the absence of an induction signal to which the inducible activating polynucleotide is sensitive, b) bringing into contact the transformed plant as defined in a) with the inducible activating signal to which the inducible activating polynucleotide is sensitive, c) recovering the mature seeds, which upon development produce exclusively plants with female flowers.

In a further embodiment, an inducible repressing regulatory polynucleotide (Pa) is used for replacing the regulatory polynucleotide naturally present in the plant, and enabling to reduce the ACCS protein level at a predetermined time.

Preferred Methods for Producing a Plant with Exclusively Female Flowers

Most preferably, the present invention relates to a method for producing a plant having exclusively female flowers, characterized in that it does consist of:

detecting the alleles (A), (a), (G) and (g) by performing the hereabove detection methods, and obtaining a plant comprising at least one copy of the allele (A) and no copy of the allele (G), by performing the selection methods or the methods for producing a transformed plant such as defined hereabove.

The plants that are obtained by means of the hereabove method have exclusively female flowers, and are therefore particularly interesting from an industrial point of view, since they are not capable of self-pollination. These plants may therefore be used in selection methods to obtain hybrid plants.

Preferred Methods for Producing a Plant Having Exclusively Hermaphroditic Flowers Most preferably, the present invention relates to a method for producing a plant having exclusively bisexual flowers, characterized in that it does consist in:

detecting the alleles (A), (a), (G) and (g) by performing the hereabove defined detection methods, and obtaining a plant that has no copy of the allele (A) and no copy of the allele (G), by implementing the selection methods or the methods for producing a transformed plant such as defined hereabove.

The plants that are obtained by means of the hereabove method have exclusively hermaphroditic flowers, and are therefore particularly interesting from an industrial point of view, since they are not capable of self-pollination. These plants may therefore be used in methods for producing pure plant lines.

Methods for Transforming Plants of the Invention

The most widely used methods for introducing nucleic acids into vegetable cells may be used in the context of the present invention.

Transforming vegetable cells may be effected using various methods such as, for example, by transferring the hereabove mentioned vectors into the vegetable protoplasts after incubation of the latter in a polyethylene glycol solution in the presence of divalent cations (Ca++), by electroporation (Fromm and al. 1985), use of a gene gun, or by cytoplasmic or nuclear microinjection (Neuhaus and al, 1987).

One of the method for transforming vegetable cells that may be used in the context of the present invention consists in transfecting vegetable cells with a bacterial host cell comprising the vector with the interesting sequence. The host cell may be *Agrobacterium tumefaciens* (An and al. 1986), or *A. rhizogenes* (Guerche and al. 1987).

Preferably, transforming vegetable cells is effected by the T-region transfer of the tumor-inducing Ti extra chromosomal circular plasmid of *A. tumefaciens*, by using a binary system (Watson and al., 1994). For this purpose, two vectors are prepared. In one of these vectors, the DNA-T region was removed by deletion, except the right and left borders, a gene marker being inserted therebetween to enable the selection within the plant cells. The second partner of the binary system is an auxiliary Ti plasmid, a modified plasmid which does not comprise any DNA-T anymore but which still comprises virulence genes vir required to transform the vegetable cell. This plasmid is maintained in *Agrobacterium*.

In a preferred embodiment, the method described by Ishida and al. (1996) may be applied for transforming dicotyledon plants. According to another procedure, the transformation is performed by means of the method described by Finer and al. (1992) with the gene gun using tungsten or gold particles.

EXAMPLES

Example 1

Identification of a Single Nucleotide Polymorphism (SNP)

Figure 1:
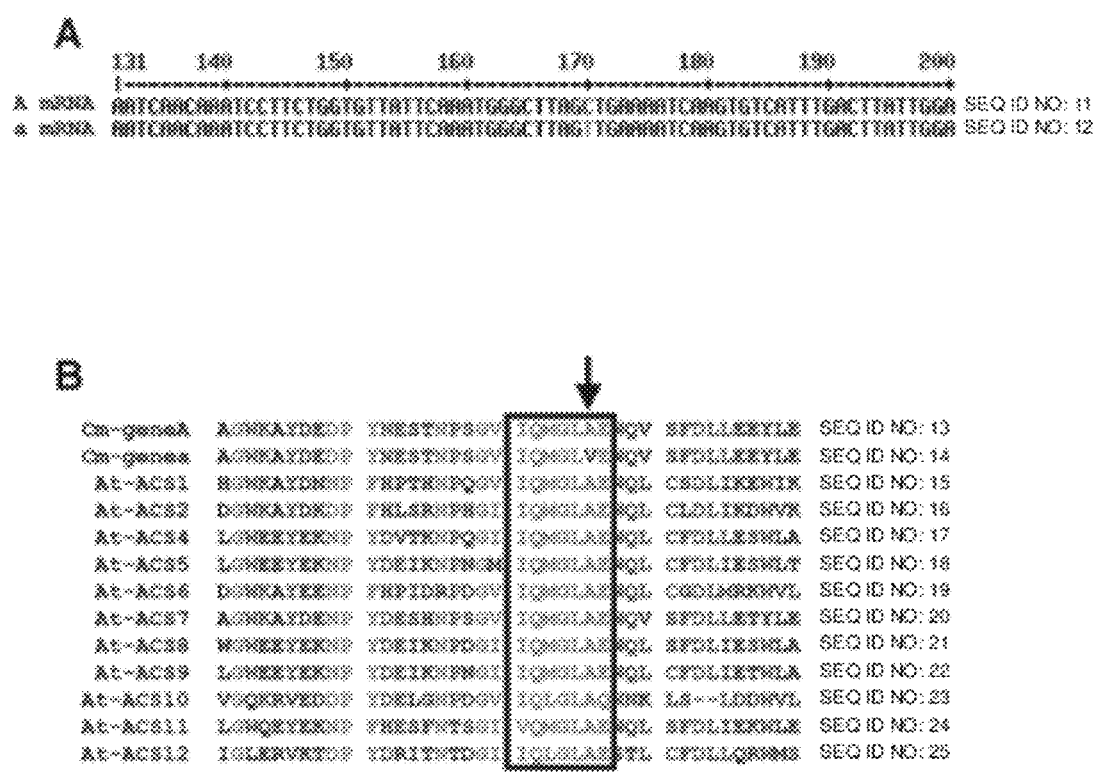

The sequence analysis of a DNA fragment comprising the promoter of the gene (A/a) region (2 kb upstream from the initiation codon) reveals a high level of polymorphism in the regulatory region at 5' and in the intron sequences, whereas only one occasional mutation in the protein coding sequence was identified (FIG. 1A). Such occasional mutation on the nucleic acid results as regards the ACCS protein polypeptide sequence in the replacement of an alanine residue at position 57 with a valine residue (FIG. 1B). By using methods for predicting amino acid substitutions, based on sequence and physical property homologies, it has been analyzed whether the occasional mutation identified in the allele a is harmful for the protein function.

The SIFT software (Ng PC and Henikoff S., 2001) does predict that Ala57Val substitution has a highly harmful effect on the function A. Moreover, crystalline structure analyses of ACC synthase in apple and tomato (Capitani and al., 2002; Huai and al., 2001) do highlight the crucial role of this amino acid.

After identification of this single nucleotide polymorphism (or SNP), analyses of haplotypes and associations in a 30 melon germplasm-collection revealed that this SNP is fully associated with the sex phenotype. All the monoecious entries do carry an alanine at position 57 whereas all the andromonoecious entries do carry a valine. No exception was found, and no other type of amino acid change at this position either.

Lastly, this single nucleotide polymorphism was analyzed in order to identify the restriction enzymes which could be used to develop a digestion method relying on the so called "Cleaved Amplified Polymorphic Sequence Markers" (CAPS). 11 has been demonstrated that the substitution of a nucleotide C with a nucleotide T causes a restriction site Alu I to be lost in the allele a.

Example 2

Spatial and Temporal Expression of the Genetic Control Element (A/a)

To analyse the expression of the genetic control element A/a in the form of the allele A, in situ hybridizations were performed by using allele A-specific probes in plants, and more precisely in male, female and bisexual plant floral meristems, of genotype AA GG, aa GG, AA gg and aa gg. In the floral meristems A, the expression is locally high and the hybridization signal is specifically detected in the female and bisexual flower carpel primordia of monoecious, andromonoecious, gynoecious and hermaphroditic plants. Referring to the various flower development stages described for cucumber (Bai and al., 2004), it appears in melon that the gene (A/a) is expressed in an early stage of the floral meristem development, before a morphological distinction may be done between male and female flowers.

In male and hermaphroditic flowers, no expression could be detected in the anthers. These results indicate that expressing the allele (A) in the female flower carpelles inhibits the stamina development. Because the recessive allele (a) in hermaphroditic flowers has the same expression profile as the allele (A) in female flowers, it may be concluded that the gene A function does depend on its tissue-expression specificity as well as on the nature of the synthesized ACCS protein.

Example 3

Transgenesis in *Arabidopsis thaliana*

The possible effects of gene A/a and ACCS protein on the flower sex phenotype and the flower architecture in plants not belonging to cucurbitaceae have been studied by transforming *Arabidopsis thaliana* with *Agrobacterium*. *Arabidopsis* transgenic plants carrying the melon allele A or a have a phenotype at the floral architecture and siliqua level. (FIGS. 2A and 2B). Indeed siliqua of *Arabidopsis* transformants are shorter than those of a wild type *Arabidopsis* plant and the flower architecture of the *Arabidopsis* transformants is highly affected. These results enable to extend the use of the melon gene (A/a) to dicotyledon plants not belonging to the cucurbitaceae family.

REFERENCE WORKS

An et al., (1986) Plant Physiol. 81, 86-91
Aoyama T et al., (1997) The Plant Journal, vol. 11 (3):605-612.
Ausubel et al., (1997) Current protocols in molecular biology
Bai et al., 2004 Planta 220: 230-240
Beaucage et al. (1981), Tetrahedron Lett., 22:1859-1862.
Berbal, 1984.
Bevan et al., Nucleic Acids Research, vol. 12:8711-8721.
Brown et al. (1979), Methods Enzymol., 68:109-151.
Causse et al. (1995) Molecular Breeding 1: 259-272.
Capitani et al., 2002 J. Biol. Chem. 51: 49735-49742
Christensen et al. (1996), Transgenic. Res., 5:213
Finer et al. (1992) Plant Cell Report, 11, 323-328
FROMM M. et al. (1990), Biotechnology, 8:833-839
GAIT (ed.), (1984). A nucleic acid Hybridization.
GORLACH J, VOLRATH S, KNAUF-BEITER G, HENGY G, BECKHOVE U, KOGEL K H, OOSTENDORP M, STAUB T, WARD E, KESSMANN H, RYALS J. (1996) Benzothiadiazole, a novel class of inducers of systemic acquired resistance, activates gene expression and disease resistance in wheat. Plant Cell 8:629-43
GLOVER (ed.), 1985. DNA Cloning: A Practical Approach, Volumes I and II Oligonucleotide Synthesis, MRL Press, Ltd., Oxford, U. K.
Guerche et al. (1987), Mol. Gen. Genet. 206, 382
HAMES and HIGGINS, 1985. A nucleic acid Hybridization: a practical approach, Hames & Higgins Ed. IRL Press, Oxford.
HAJDUKIEWICZ, P. SVAB. Z. AND MALIGA P. Plant Mol. Biol. 25 (6), 989-994 (1994). Huai et al., 2001 J; Biol. Chem. 41: 38210-38216
Ishida et al. (1996) Nature biotechnology 14, 745-750
JEFFERSON, 1987, Plant Molecular Biology Reporter, vol. 5:387-405.
Kay et al., (1987) Science 236, 4805
Kahana, A., Silberstein, L., Kessler, N., Goldstein, R. S, and Perl-Treves, R. (2000) expression of ACC oxidase genes differs among sex genotypes and sex phases in cucumber. Plant Mol. Biol. November; 41 (4): 517-528.
Kamachi, S., Sekimoto, H., Kondo, N. & Sakai, S., (1997). Cloning of a cDNA for a 1-aminocyclopropane-1-carboxylate synthase that is expressed during development of female flowers at the apices of *Cucumis sativus* L. The Plant Cell Physiol., 38:1197-206.
Kohler G and Milstein C, (1975), Nature, volume 256:495
KOOTER, J M., MATZKE, M A., AND MEYER, P. (1999) Listening to the silent genes: transgene silencing, gene regulation and pathogen control. Trends Plant Sci. 4, 430-437
Kozbor et al., (1983), Hybridoma, vol. 2 (1):7-16.
Leger O J et al., (1997), Hum Antibodies, vol. 8 (1):3-16
Martineau P et al., (1998), J. Mol. Biol. vol. 280(1):117-127.
Martinez, A., Sparks, C., Hart, C A., tompson, J., and Jepson, I. (1999) Ecdysone agonist inducible transcription in transgenic tobacco plants. Plant J. 19:97-106
McNELLIS T W, 1998, The Plant Journal, vol. 14 (2): 247-257
Molina A, Hunt M D, Ryals J A (1998) Impaired fungicide activity in plants blocked in disease resistance signal transduction. Plant Cell 10:1903-14 NARANG et al. (1979), Methods Enzymol., 68: 90-98.
Neuhaus et al., (1987). Theor. Appl. Genet. 75(1), 30-36
Ng PC and Henikoff S. (2001) Genome Res. 11 (5):863-874
Reinmann K A et al. (1997), Aids Res. Hum retroviruses, vol. 13 (11):933-943.
Ridder R. et al., (1995), Biotechnology (NY), vol. 13 (3):255-260.
SALTER MG et al., 1998, vol. 16 (1): 127-132
Risser, G. and Rode, J. C., 1979. Induction par le nitrate d'argent de fleurs staminées chez des plantes gynoïques de melon (*Cucumis melo* L.). Annales de l'Amélioration des Plantes, 29:349-352.
Rudich, J., Halevy, A. H. and Kedar, N., 1969. Increase of femaleness of three cucurbits by treatment with Ethrel, an ethylene-releasing compound. Planta, 86:69-76.
Sambrook et al., (2001), Molecular Cloning A-laboratory manual
Sanchez Pescador, (1988), J. Clin. Microbiol., 26 (10):1934-1938.
Urdea et al. (1988), Nucleic Acids Research, 11:4937-4957.
WASSENEGGER, M., AND PÉLISSIER, T. (1998) A model for RNA-mediated gene silencing in higher plants Plant Mol. Biol. 37, 349-362
Watson et al. (1994) ADN recombinant, Ed. De Boek Universite, 273-292 YANG F. MOSS LG, PHILIPS GN JR. Nat. Biotechnol. 1996 Oct. 14(10):1246-51.
YANG T T, CHENG L. KAIN S R, Nucleic acids Res. 1996, Nov. 15; 24(22):4592-3.

The invention claimed is:

1. An isolated nucleic acid molecule, comprising, from the 5' end to the 3' end:
   (i) a sequence having at least 95% identity with the polynucleotide extending from nucleotide 5907 to nucleotide 6086 of SEQ ID NO:1,
   (ii) a sequence having at least 95% identity with the polynucleotide extending from nucleotide 6181 to nucleotide 6467 of SEQ ID NO:1, and
   (iii) a sequence having at least 95% identity with the polynucleotide extending from nucleotide 7046 to nucleotide 7915 of SEQ ID NO:1,
wherein the nucleic acid molecule encodes an active 1-aminocyclopropane-1-carboxylate synthase (ACCS) protein having enzyme activity to transform S-adenosylmethionine (SAM) to 1-aminocyclopropane-1-carboxylate (ACC).

2. The nucleic acid molecule according to claim 1, comprising SEQ ID NO:1.

3. The nucleic acid molecule according to claim 1, further comprising a nucleotide sequence extending from nucleotide 1 to nucleotide 5906 of SEQ ID NO:1.

4. A recombinant vector, comprising the nucleic acid molecule as defined in claim 1.

5. An isolated host cell transformed with the nucleic acid molecule as defined in claim 1.

6. The host cell according to claim 5, wherein the host cell is a plant cell.

7. A plant comprising the host cell as defined in claim 6.

8. A transformed plant, comprising a plurality of host cells as defined in claim 6.

9. The nucleic acid molecule according to claim 1, further comprising a functional regulatory polynucleotide (Pa) or promoter which enables the ACCS protein to be expressed in dicotyledon plants.

10. The nucleic acid molecule according to claim 1, wherein nucleotide 6076 is C.

11. The host cell according to claim 6, wherein the host cell is a plant cell belonging to the cucurbitaceae family.

12. The nucleic acid molecule according to claim 1, wherein a plant transformed with said nucleic acid molecule produces female flowers.

13. The nucleic acid molecule according to claim 1, wherein a plant transformed with said nucleic acid molecule has a monoecious or a gynoecious phenotype.

* * * * *